US012636384B2

(12) United States Patent
Zheng et al.

(10) Patent No.: US 12,636,384 B2
(45) Date of Patent: May 26, 2026

(54) NANOEMULSION WITH PORPHYRIN SHELL

(71) Applicant: UNIVERSITY HEALTH NETWORK, Toronto (CA)

(72) Inventors: Gang Zheng, Toronto (CA); Juan Chen, Toronto (CA); Wenxiu Hou, Shanghai (CN); Jiachuan Bu, Toronto (CN)

(73) Assignee: UNIVERSITY HEALTH NETWORK, Toronto (CA)

( * ) Notice: Subject to any disclaimer, the term of this patent is extended or adjusted under 35 U.S.C. 154(b) by 779 days.

(21) Appl. No.: 17/608,911

(22) PCT Filed: May 6, 2020

(86) PCT No.: PCT/CA2020/050617
§ 371 (c)(1),
(2) Date: Nov. 4, 2021

(87) PCT Pub. No.: WO2020/223813
PCT Pub. Date: Nov. 12, 2020

(65) Prior Publication Data
US 2022/0296731 A1     Sep. 22, 2022

Related U.S. Application Data

(60) Provisional application No. 62/844,543, filed on May 7, 2019.

(51) Int. Cl.
*A61K 9/00*      (2006.01)
*A61K 9/51*      (2006.01)
*A61K 31/337*    (2006.01)
*A61K 41/00*     (2020.01)
*A61K 49/00*     (2006.01)

(52) U.S. Cl.
CPC ........ *A61K 49/0065* (2013.01); *A61K 9/5123* (2013.01); *A61K 31/337* (2013.01); *A61K 41/0071* (2013.01); *A61K 49/0036* (2013.01)

(58) Field of Classification Search
CPC ................................................ A61K 49/0065
See application file for complete search history.

(56) References Cited

U.S. PATENT DOCUMENTS

2016/0158153 A1     6/2016  Faivre et al.

FOREIGN PATENT DOCUMENTS

| CN | 105408015 A | 3/2016 | |
| CN | 106659684 A | 5/2017 | |
| WO | WO-0074653 A1 * | 12/2000 | ........... A61K 31/337 |
| WO | 2010045292 A2 | 4/2010 | |

(Continued)

OTHER PUBLICATIONS

Huihui, et al., "A TPGS-incorporating nanoemulsion of paclitaxel circumvents drug resistance in breast cancer"; International Journal of Pharmaceutics. 2014, 471, 206-213.

(Continued)

*Primary Examiner* — Paul W Dickinson
(74) *Attorney, Agent, or Firm* — NORTON ROSE FULBRIGHT CANADA LLP

(57) ABSTRACT

There is described herein a nanoparticle comprising an outer shell comprising a porphyrin salt, an expanded porphyrin salt or an analog of porphyrin salt, around an inner oil core.

31 Claims, 24 Drawing Sheets

(56)                    References Cited

FOREIGN PATENT DOCUMENTS

| WO | 2015192215 A1 | 12/2015 |
| WO | 2019010329 A1 | 1/2019 |

OTHER PUBLICATIONS

Jaiswal, et al., "Nanoemulsion: an advanced mode of drug delivery system"; 3 Biotech (2015), 5:123-127.

Dehelean, et al., "Anti-Angiogenic Effects of Betulinic Acid Administered in Nanoemulsion Formulation Using Chorioallantoic Membrane Assay"; Journal of Biomedical Nanotechnology, (2011), vol. 7, 1-8.

Ganta, et al., "Nanoemulsions in Translational Research—Opportunities and Challenges in Targeted Cancer Therapy"; AAPS PharmSciTech, vol. 15, No. 3, Jun. 2014.

Rai, et al., "Nanoemulsion as pharmaceutical carrier for dermal and transdermal drug delivery: Formulation development, stability issues, basic considerations and applications"; Journal of controlled release: official journal of the Controlled Release Society 2018, 270, 203-225.

Singh, et al., "Nanoemulsion: Concepts, development and applications in drug delivery"; Journal of controlled release, 2017, 252, 28-49.

Silva, et al., "Current Trends in Cancer Nanotheranostics: Metallic, Polymeric, and Lipid-Based Systems"; Pharmaceutics 2019, 11. doi: 10.3390/pharmaceutics11010022.

Fernandes, et al., "Synthesis of Stable Multifunctional Perfluorocarbon Nanoemulsions for Cancer Therapy and Imaging"; Langmuir 2016, 32, 10870-10880.

Gianella, et al., "Multifunctional Nanoemulsion Platform for Imaging Guided Therapy Evaluated in Experimental Cancer"; Multifunctional Nanoemulsion 2011 Vol. 5, No. 6, 4422-4433.

Ganta, et al., "Development of EGFR-Targeted Nanoemulsion for Imaging and Novel Platinum Therapy of Ovarian Cancer"; Pharmaceutical research 2014, 31, 2490-2502.

Patel, et al., "Design, Synthesis, and Characterization of Folate-Targeted Platinum-Loaded Theranostic Nanoemulsions for Therapy and Imaging of Ovarian Cancer"; Molecular pharmaceutics 2016, 13, 1996.

Lee, et al., "Interaction of Melittin Peptides with Perfluorocarbon Nanoemulsion Particles"; The journal of physical chemistry. B 2011, 115, 15271-15279.

Patel, et al., "In Vitro and In Vivo evaluation of a novel folate-targeted theranostic nanoemulsion of docetaxel for imaging and improved anticancer activity against ovarian cancers"; Cancer biology & therapy 2018, 19, 554-564.

Patel, et al., "Theranostic nanoemulsions for macrophage COX-2 inhibition in a murine inflammation model"; Clinical immunology 2015, 160, 59-70.

Jarzyna, et al., "Iron oxide core oil-in-water emulsions as a multifunctional nanoparticle platform for tumor targeting and imaging"; Biomaterials 2009, 30, 6947-6954.

Yan, et al., "Protoporphyrin IX (PpIX)-Coated Superparamagnetic Iron Oxide Nanoparticle (SPION) Nanoclusters for Magnetic Resonance Imaging and Photodynamic Therapy"; Advanced functional materials 2018, 28, 1707030.

Nel, et al., "Toxic Potential of Materials at the Nanolevel"; science 2006, 311, 622-627.

Dobrovolskaia, et al., "Immunological properties of engineered nanomaterials"; Nature nanotechnology 2007, 2, 469.

Rajora, et al., "Advancing porphyrin's biomedical utility via supramolecular chemistry"; Chemical Society Reviews 2017, 46, 6433-6469.

Li, et al., "A smart and versatile theranostic nanomedicine platform based on nanoporphyrin"; Nature communications 2014, 5, 4712.

Zhou, et al., "Porphyrin-loaded nanoparticles for cancer theranostics"; Nanoscale 2016, 8, 12394-12405.

Cui, et al., "Organized Aggregation of Porphyrins in Lipid Bilayers for Third Harmonic Generation Microscopy"; Angewandte Chemie International Edition 2015, 54, 13928-13932.

Tan, et al., "Triglycerideewater emulsions stabilised by starch-based nanoparticles"; Food Hydrocolloids 2014, 36, 70-75.

Huynh, et al., "In situ conversion of porphyrin microbubbles to nanoparticles for multimodality imaging"; Nature nanotechnology 2015, 10, 325.

Khurana, et al., "Nanoemulsion based gel for transdermal delivery of meloxicam: Physico-chemical, mechanistic investigation"; Life sciences 2013, 92, 383-392.

Lovell, et al., "Porphysome nanovesicles generated by porphyrin bilayers for use as multimodal biophotonic contrast agents"; Nature materials 2011, 10, 324.

Kuen et al., "Formation of Core/Shell Nanoparticles with a Lipid Core and Their Application as a Drug Delivery System"; Biomacromolecules 2005, 6, 1062-1067.

Kuen, et al., Core/Shell Nanoparticles with Lecithin Lipid Cores for Protein Delivery; Biomacromolecules 2006, 7, 2362-2367.

Overchuk, et al., "Tailoring Porphyrin Conjugation for Nanoassembly-Driven Phototheranostic Properties"; ACS Nano 2019, 13, 4560-4571.

\* cited by examiner

|  | PTX (mg) | Pyro(μmol) :oil (μL) | Z-Average (nm) | PDI | EE(%) | LD(%) |
|---|---|---|---|---|---|---|
| H0 | 0 | 4:20 | 105.2±0.4 | 0.131±0.006 | 0 | 0 |
| H1 | 0.2 | 4:20 | 122.5±0.6 | 0.161±0.111 | 97.2±1.9 | 0.82±0.07 |
| H2 | 0.4 | 4:20 | 121.5±0.3 | 0.179±0.006 | 92.9±5.6 | 1.55±0.15 |
| H3 | 0.8 | 4:20 | 129.5±0.2 | 0.209±0.007 | 85.6±3.5 | 3.29±0.16 |
| H4 | 1.2 | 4:20 | 139.1±0.1 | 0.222±0.008 | 70.9±3.6 | 4.02±0.22 |

Figure 22

NANOEMULSION WITH PORPHYRIN SHELL

RELATED APPLICATIONS

This application claims priority to U.S. Provisional Application No. 62/844,543, filed May 7, 2019 incorporated herein by reference.

FIELD OF THE INVENTION

The invention relates to nanoemulsions, and more specifically to nanoemulsions comprising porphyrins.

BACKGROUND OF THE INVENTION

Typical nanoemulsions are oil-in-water or water-in-oil droplets with size ranging from 20-200 nm, and often stabilized by surfactants.[1] Nanoemulsions are favourable for drug delivery given their easy and scalable production and promising lipophilic compounds-loading affinity,[2] thus leading to many FDA approved products, such as Liple®, Cleviprex®, and Lipfen®.[2b] As multimodal and theranostic techniques are gaining popularity in cancer Nanomedicine,[3] many multifunctional and/or targeted nanoemulsions have been investigated[4] by stacking together different functional components either via encapsulation or surface functionalization approaches, resulting in complicated architectures and often requiring complex procedure for fabrication.[4c, 5] Surfactants play indispensable role in classical nanoemulsion construction, therefore account for a major weight fraction that unfavourably limit drug or imaging agents loading capacity[6] and lead to undesirable toxic or immunogenic response in systemic delivery.[7] Porphyrins are biodegradable, organic heterocyclic molecules with red or near infrared absorption properties, high singlet oxygen ($^1O_2$) quantum yields and metal chelation properties, thus are well-suited components for multimodal imaging and therapy.[8]

SUMMARY OF THE INVENTION

In an aspect, there is provided a nanoparticle comprising an outer shell comprising a porphyrin salt, an expanded porphyrin salt or an analog of porphyrin salt, around an inner oil core.

In an aspect, there is provided a composition comprising the nanoparticle described herein and water. The composition is preferably surfactant free. In some embodiments, the nanoparticle is in PBS. In some embodiments, the composition is a nanoemulsion.

In an aspect, there is provided a method of preparing the composition described herein, comprising hydrating a film comprising a mixture of the porphyrin salt, the expanded porphyrin salt or the porphyrin isomer salt with the oil.

In an aspect, there is provided a method of performing fluorescence imaging on a target area in a subject comprising: providing the composition described herein; administering the composition to the subject; and imaging the target area.

In an aspect, there is provided a method of photoacoustic imaging a target area in a subject, comprising: providing the composition of described herein; administering the composition to the subject; and measuring and/or detecting a photoacoustic signal at the target area.

In an aspect, there is provided a method of photodynamic therapy of a target area in a subject, comprising: providing the composition described herein; administering the composition to the subject; and irradiating the target area with light of a wavelength that excites the composition to produce radicals and/or reactive oxygen species.

In an aspect, there is provided a method delivering a diagnostic or therapeutic agent to a subject comprising administering to the subject the composition described herein, wherein the nanoparticle has been co-loaded with said diagnostic or therapeutic agent.

In an aspect, there is provided a use of the composition described herein for performing imaging.

In an aspect, there is provided a use of the composition described herein for delivery of a diagnostic or therapeutic agent to a subject, wherein the nanoparticle has been co-loaded with said diagnostic or therapeutic agent.

BRIEF DESCRIPTION OF FIGURES

These and other features of the preferred embodiments of the invention will become more apparent in the following detailed description in which reference is made to the appended drawings wherein:

FIG. 22. Table showing Particle Size, drug encapsulation efficiency and drug-loading capacity of the Paclitaxel loading PyroNewPS. Entrapment Efficiency (EE) (%)=weight of PTX in Nanoemulsions/weight of PTX initially feeding in formulation×100%;

Drug-Loading capacity (DL) (%)=weight of PTX in Nanoemulsions/weight of final Nanoemulsions× 100%.

Figure 23:
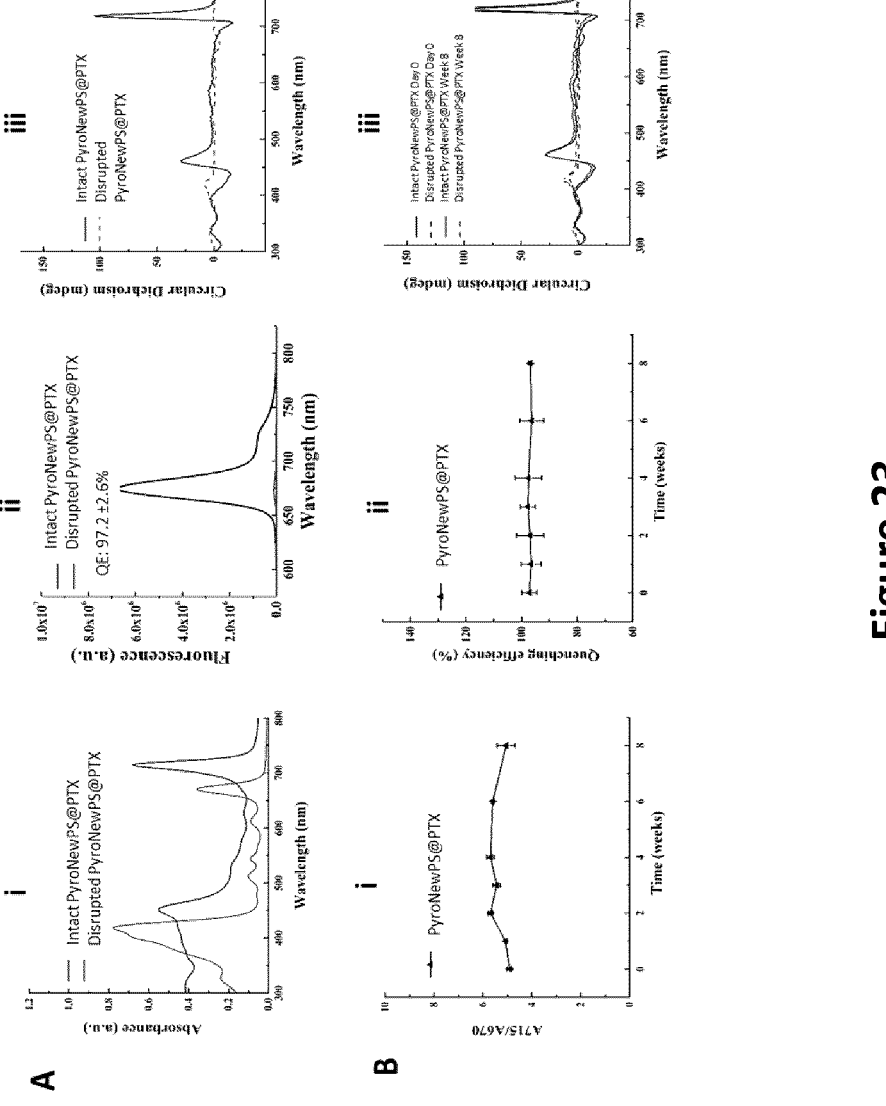

FIG. 23. The optical characters of fresh prepared PyroNewPS@PTX (A). (Ai) absorption spectra; (Aii) Fluorescence quenching efficiency (QE); (Aiii) Circular Dichroism spectra. The stability measurement of PyroNewPS@PTX during 8-weeks storage (B). (Bi) The ratio changes of J-peak absorption/monomer peak absorption; (Bii) The fluorescence quenching efficiency changes during storage; (Biii) Circular Dichroism spectra changes during storage.

Figure 24:
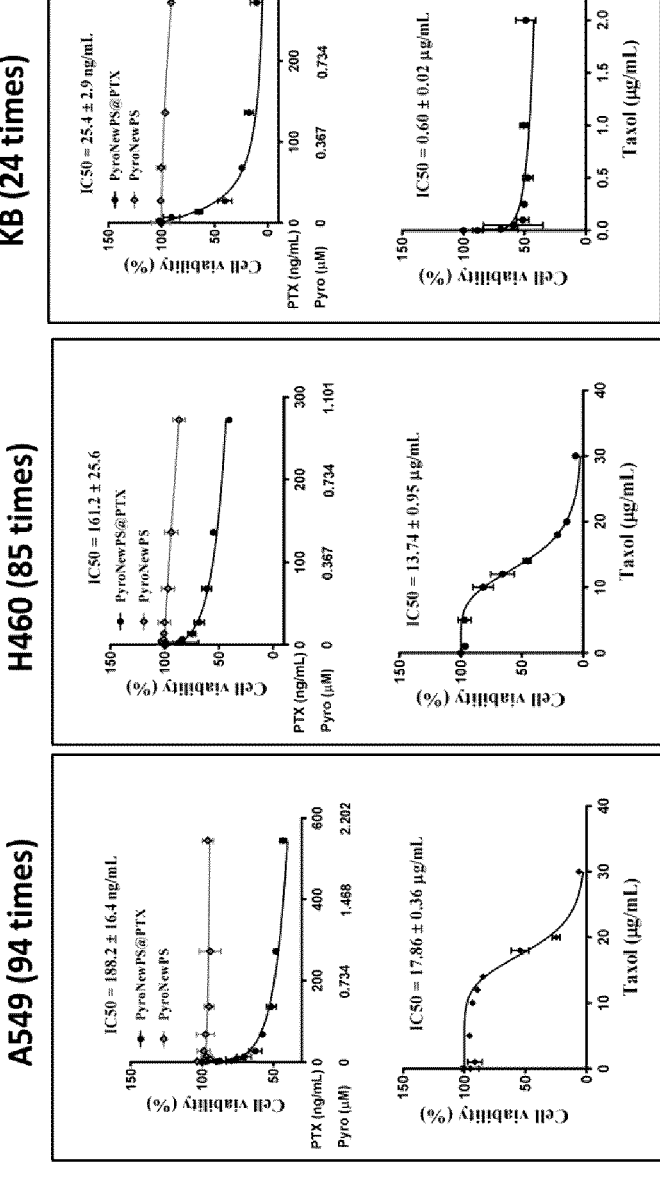

FIG. 24. In vitro cytotoxicity evaluation using PyroNewPS@PTX or Taxol against A546 cells, H460 cells and KB cells. PyroNewPS at the same pyro concentration was used as an empty vehicle control that did not induce significant cytotoxicity at the experimental concentration for all cells. IC50 value was calculated as the lethal PTX concentrations that resulted in 50% of cells growth. All IC50 values obtained were the mean value from three independent MTT assays. Each MTT assay data shown were mean±SD (n=4).

DETAILED DESCRIPTION

In the following description, numerous specific details are set forth to provide a thorough understanding of the invention. However, it is understood that the invention may be practiced without these specific details.

A nanoemulsion with porphyrin shell (NewPS) was created by the self-assembly of porphyrin salt around oil core. The NewPSs have ~100 nm spherical structure with excellent colloidal stability against radical changes in temperature, mechanical agitation, pH and in serum. The NewPS system is amenable to different porphyrin salts (mono-sodium or tris-sodium salt) and oils (low or high density), and is capable of co-loading of chemotherapeutics (paclitaxel). Porphyrin salt shell is essential for the nanostructure construction and provides a porphyrin-dependent optical tunability. In the NewPS made of pyropheophorbide a monosalt (PyroNewPS), an ordered J-aggregation of porphyrin shell was formed to produce a narrow, red-shifted (from 671 nm to 715 nm) Q-band with increased absorbance. This enabled spectrally distinct photoacoustic imaging (at 715 nm by intact NewPS) and fluorescence increase (at 671 nm from dissociated NewPS,) to track the NewPS accumulation and disruption in KB tumors mouse model and to guide effective PDT. Swapping the oil core with Lipiodol® afforded additional CT contrast, whereas loading paclitaxel into NewPS lends to drug delivery capability. This simple two-component NewPS offers a new nanoplatform for multimodal cancer imaging, phototherapy and imaging-guided drug delivery.

In an aspect, there is provided a nanoparticle comprising an outer shell comprising a porphyrin salt, an expanded porphyrin salt or an analog of porphyrin salt, around an inner oil core.

In some embodiments, the outer shell is a porphyrin salt. Preferably, the porphyrin salt is a salt of a hematoporphyrin (e.g. Hemin), a protoporphyrin (protoporphyrin IX), a pyropheophorbide a, a bacteriochlorophyll derivative (e.g. Bacteriopheophorbide), a chlorophyll a, a tetraphenylporphyrin derivative, a benzoporphyrin derivative, a verpetorfin, a chlorin, a benzochlorin, a naphthochlorins, a rhodin, a keto chlorin, an azachlorin, a bacteriochlorin, a tolyporphyrin, a benzobacteriochlorin, a deuteroporphyrin, a pemptoporphyrin a phylloerythrin, a porphine, or apurpurin 18. Further preferably, the porphyrin salt is a carboxylate or sulfonate salt.

In some embodiments, the outer shell is an expanded porphyrin salt. Preferably, the expanded porphyrin salt is a salt of a texaphyrin, a sapphyrin or a hexaphyrin.

In some embodiments, the outer shell is an analog of porphyrin salt. Preferably, the analog of porphyrin salt is a salt of a porphycene, an inverted porphyrin, a phthalocyanine, a naphthalocyanine, a BODIPY dye, or a cyanine dye. In some embodiments, the analog of porphyrin salt is zinc(II) phthalocyanine mono-sodium salt, aza-BODIPY mono-sodium salt, or ICG cyanine salt.

In some embodiments, the porphyrin salt is pryopheophorbide a mono-sodium salt.

In some embodiments, the porphyrin salt is chlorin e6 tris-sodium salt.

In some embodiments, the porphyrin salt is bacteriopheophorbide a mono-sodium salt.

In some embodiments, the oil is a modified or hydrolyzed vegetable oil, a natural di- or triglyceride; a medium chain triglyceride; a semi synthetic medium chain triglyceride containing compound (e.g. Gelucire), a digestible or non-digestible oil or fat.

In some embodiments, the oil is olive oil, corn oil, soybean oil, palm oil, animal fat, Lipidol oil, or mineral oil. Alternatively, in separate embodiments the oil is glyceryl trioctanoate oil, or lipidol.

In some embodiments, the nanoparticle is 50 nm-200 nm in diameter. In other embodiments, the nanoparticle is 80 nm-150 nm in diameter or about 100 nm in diameter.

A wide variety of hydrophobic bioactive or therapeutic agents, pharmaceutical substances, or drugs can be encapsulated within the core.

In some embodiments, the nanoparticle is co-loaded with a therapeutic or diagnostic agent.

The term "therapeutic agent" is art-recognized and refers to any chemical moiety that is a biologically, physiologically, or pharmacologically active substance. Examples of therapeutic agents, also referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject.

A "diagnostic" or "diagnostic agent" is any chemical moiety that may be used for diagnosis. For example, diagnostic agents include imaging agents, such as those containing radioisotopes such as indium or technetium; contrasting agents containing iodine or gadolinium; enzymes such as horse radish peroxidase, GFP, alkaline phosphatase, or β-galactosidase; fluorescent substances such as europium derivatives; luminescent substances such as N-methylacrydium derivatives or the like.

In one embodiment, the therapeutic agent is a chemotherapy agent, preferably a taxane, more preferably paclitaxel. In other embodiments, the agent is docetaxel, or 1,1'-dioctadecyl-3,3,3',3'-tetramethylindotricarbocyanine iodide bis-oleate (DiR-BOA).

In some embodiments, the loading capacity is about 10%, 20%, 30%, 40%, 50%, 60%, 70%, 80%, or 85%.

In an aspect, there is provided a composition comprising the nanoparticle described herein and water. The composition is preferably surfactant free. In some embodiments, the nanoparticle is in PBS. In some embodiments, the composition is a nanoemulsion.

In some embodiments, the ratio of porphyrin (P) to oil (O) volume (mol/L) is greater than 2:20. Preferably, the P/O ratio is 2:20 to 5:20 and more prefereably, about 4:20.

In an aspect, there is provided a method of preparing the composition described herein, comprising hydrating a film comprising a mixture of the porphyrin salt, the expanded porphyrin salt or the porphyrin isomer salt with the oil.

In an aspect, there is provided a method of performing fluorescence imaging on a target area in a subject comprising: providing the composition described herein; administering the composition to the subject; and imaging the target area.

In an aspect, there is provided a method of photoacoustic imaging a target area in a subject, comprising: providing the composition of described herein; administering the composition to the subject; and measuring and/or detecting a photoacoustic signal at the target area.

In an aspect, there is provided a method of photodynamic therapy of a target area in a subject, comprising: providing the composition described herein; administering the composition to the subject; and irradiating the target area with light of a wavelength that excites the composition to produce radicals and/or reactive oxygen species.

In an aspect, there is provided a method delivering a diagnostic or therapeutic agent to a subject comprising administering to the subject the composition described herein, wherein the nanoparticle has been co-loaded with said diagnostic or therapeutic agent.

In an aspect, there is provided a use of the composition described herein for performing imaging.

In some embodiments, the imaging is for breast imaging, tumour imaging, carotid neovascularisation imaging, or endoscopic imaging.

In an aspect, there is provided a use of the composition described herein for delivery of a diagnostic or therapeutic agent to a subject, wherein the nanoparticle has been co-loaded with said diagnostic or therapeutic agent.

The advantages of the present invention are further illustrated by the following examples. The examples and their particular details set forth herein are presented for illustration only and should not be construed as a limitation on the claims of the present invention.

EXAMPLES

Methods and Materials

NewPS were formed by hydration of film of porphyrin-salt and oil, subjected to homogenize by high energy microfluidic method. Nanosizer ZS90 (Malvern Instruments) and Transmission electron microscope with 2% uranyl acetate negative staining were carried to measure the size, zeta and morphology of NewPS. Fluorescence spectra and self-quenching were characterized using a Fluoromax fluorometer (Horiba Jobin Yvon) with excited at 410 nm and emission was collected from 600 nm to 800 nm. The fluorescence quenching efficacy (%) was determined by the ratio of the summary fluorescence signal of intact NewPS from 600 nm to 800 nm to that of disrupted NewPS. The J-815 Circular Dichroism Spectrometer (JASCO) was used to collect the CD spectra of NewPS. PDT and singlet oxygen generation that was measured by singlet oxygen sensor green (SOSG) method were performed with 671 nm laser irradiation (DPSS LaserGlow Technologies, Toronto, Canada). Fluorescence and photoacoustic imaging were conducted on the Vevo 2100 LAZR photoacoustic imaging system (FUJIFILM VisualSonics, Toronto, ON) and the Maestro imaging system (CRI Maestro, USA) respectively. The CT imaging was conducted on GE eXplore Locus Ultra MicroCT and data was analysed by Siemens Inveon Research Workplace 4.0

Results and Discussion

Figure 1:
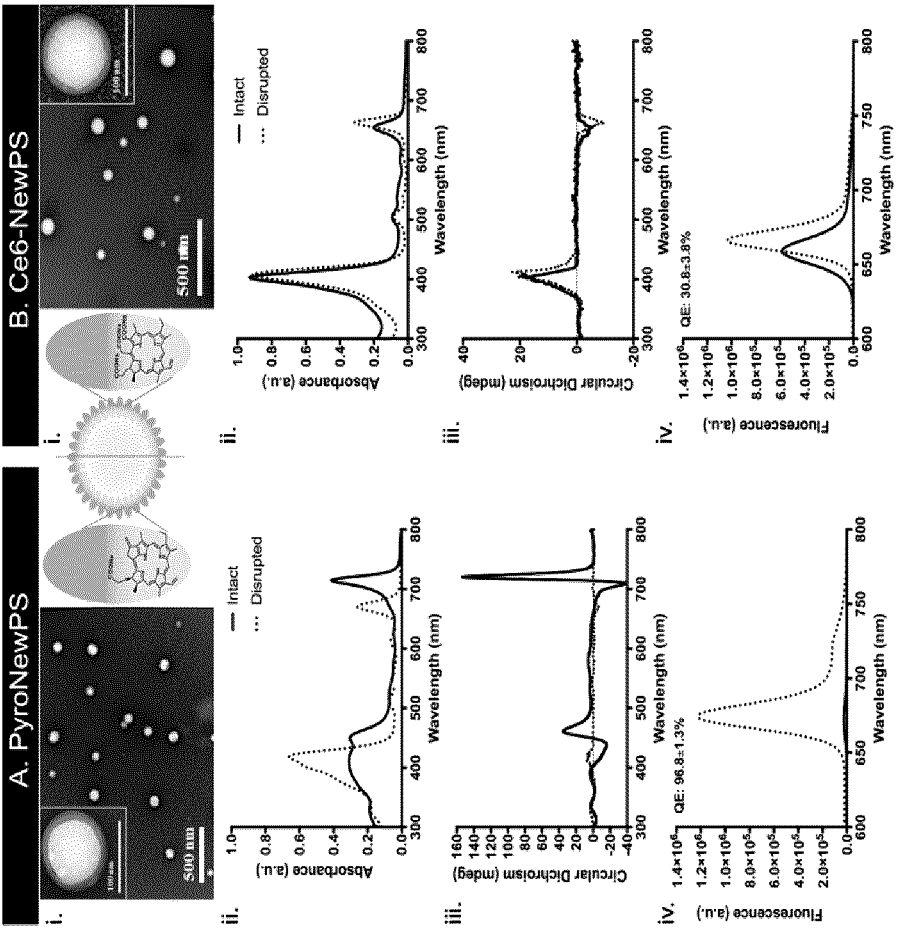
FIG. 1. (A) The scheme of NewPS, molecular structures of Pyro-salt and Ce6-salt, and the TEM images of the corresponding PyroNewPS (Ai) and Ce6-NewPS (Bi). The charactrization of PyroNewPS (B) and Ce6-NewPS, absoption spectra (Aii,Bii), CD spectra (Aiii, Biii) and fluorescence spctra (Aiv, Biv).

Herein, we created a nanoemulsion with a porphyrin shell (NewPS) as a novel surfactant-free oil-in-water nanoplatform (FIGS. 1 Ai& Bi). The NewPS was a self-assembly of porphyrin salt molecules around an oil core, resulting in a simple two-component architecture with multifunctionality for imaging and phototherapy. We have demonstrated that the amphiphilic porphyrin salt shell stabilized the oil core to offer monodispersed spherical nanoemulsion with excellent colloidal stability, whereas the oil core also gave an amiable matrix for efficient encapsulation of hydrophobic molecules (e.g. paclitaxel), thus enabling a multifunctional nanoplatform for multimodal cancer imaging, phototherapy and imaging-guided drug delivery.

Figure 5:
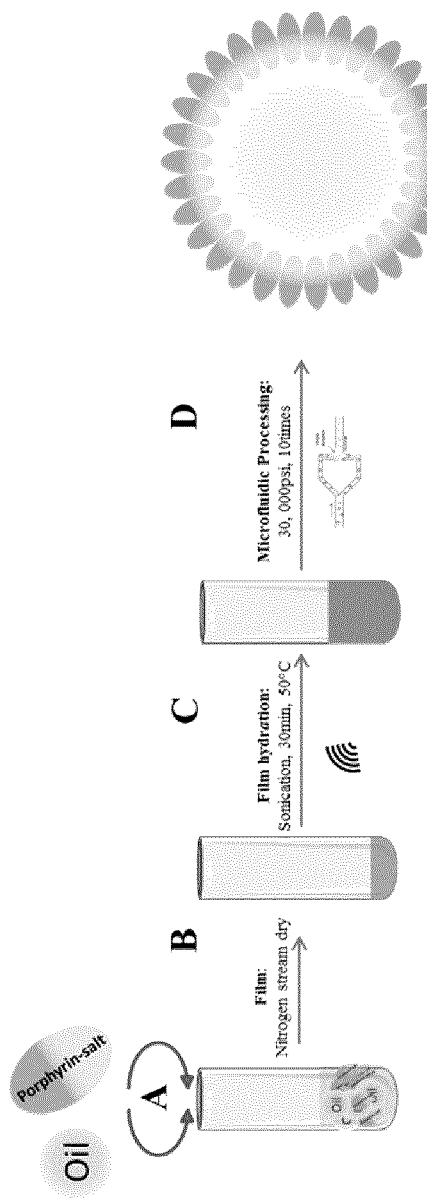
FIG. 5. The Schematic outline of the preparation of NewPS. Porphyrin-salt and oil were dissolved in $CHCl_3$ and MeOH ($9:1=CHCl_3:MeOH$) (A), dried under $N_2$ stream>3 h (B). PBS (3 mL) was added and the film was bath sonicated at 50° C. for 30 min until the solution was clear (C). The solution was passed through a microfluidizer at 30,000 psi for 10 times (D).
Figure 6:
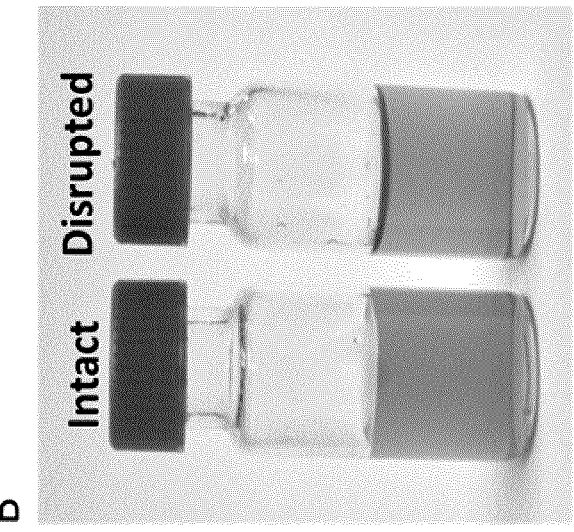
FIG. 6. (A) The DLS profile of PyroNewPS; (B) the photos of the PyroNewPS versus its nanostructure-disrupted sample in 1% (v/v %) Triton X-100.
Figure 6:
Figure 6:
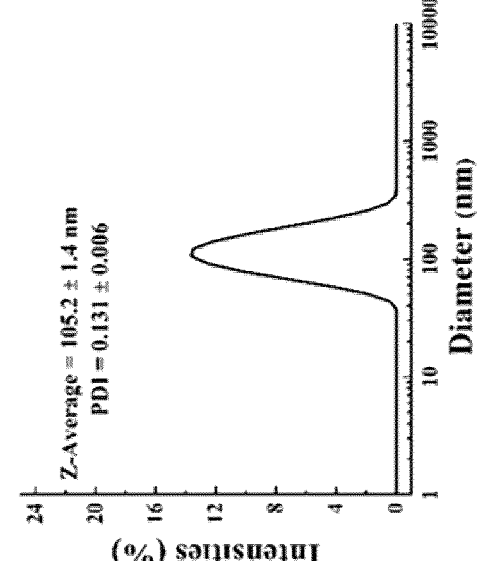
Figure 7:
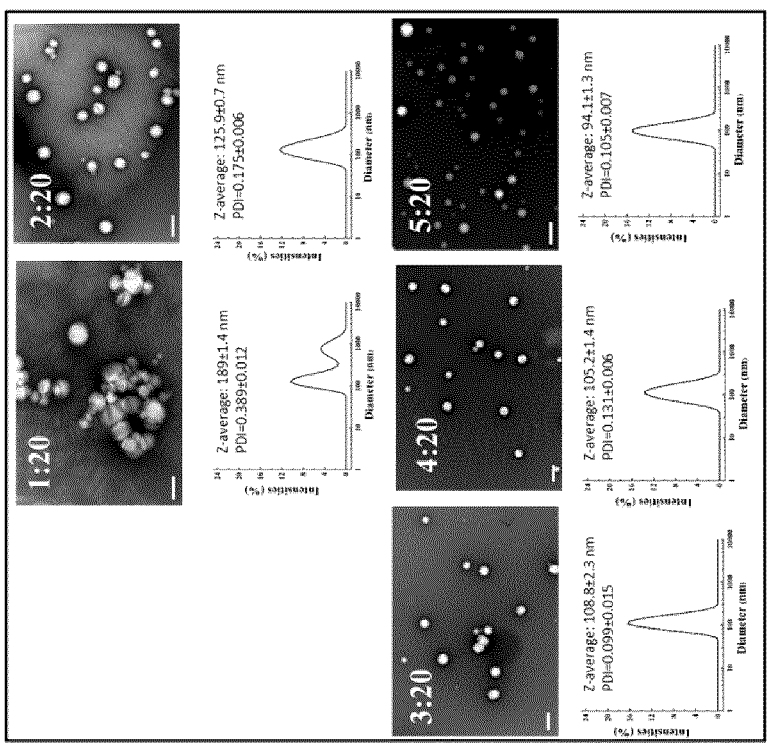
FIG. 7. To optimize the PyroNewPS formulation, a various ratio of Pyro content to oil volume (ratio of mol/L, indexed as P/O), was applied for formulation preparation. (A) The size, morphology, zeta potential of various PyroNewPSs with different P/O; (B) TEM images and dynamic light scattering (DLS) profiles of these PyroNewPSs with the corresponding P/O, scale bar=200 nm. The results showed that with increase of Pyro content (P/O from 1:20 to 2:20), the NewPSs' size was significantly decreased from 190 nm to 139 nm while the size distribution tuning to narrow from 0.39 to 0.18. Further increasing P/O ratio from 2:20 did not significantly change particles' size and PDI (size around 100 nm with PDI around 0.1). In addition, obvious particles' aggregate and polydispersity were observed for PyroNewPS at P/O ratio of 1:20, but not for NewPSs with P/O ratio 2:20 those showed monodispersed and narrow size distribution. These data together suggested that a sufficient amount of Pyro-salt (P/O>2:20) is required for forming stable porphyrin shell of NewPS.
Figure 7:
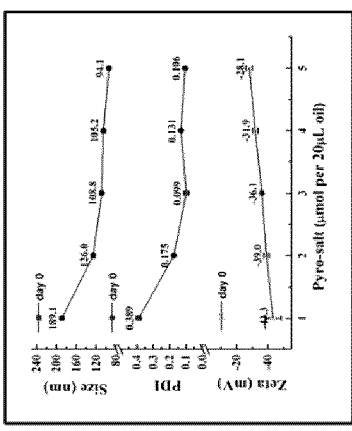
Figure 8:
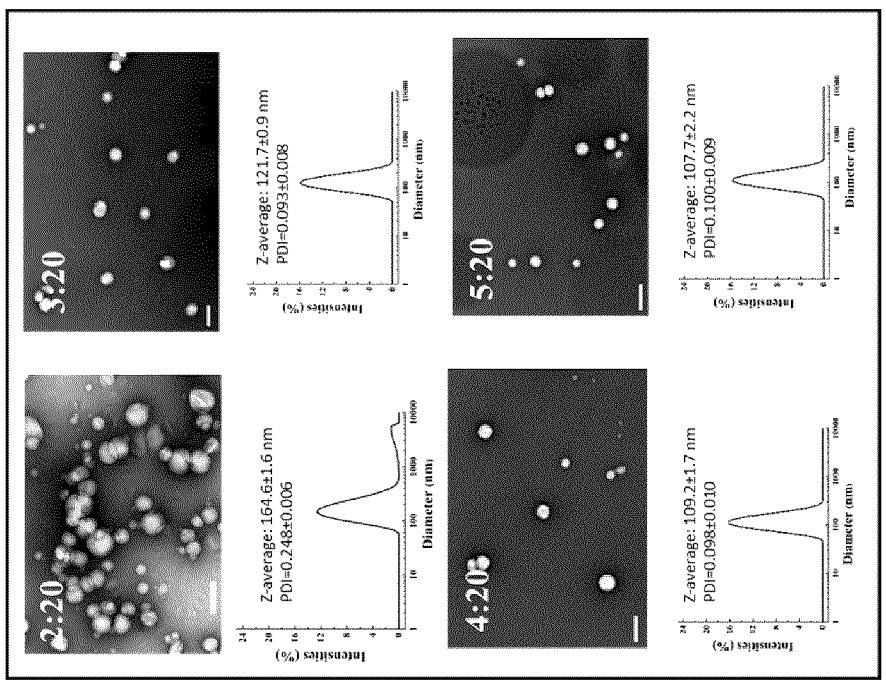
FIG. 8. The storage ability at 4° C. of PyroNewPS with P/O ratios from 2:20 to 5:20 was analyzed by their size and PDI change within 8 weeks (A) and TEM images and DLS profiles after storage for 8 weeks (B). Scale bar=200 nm. Good stability was demonstrated for PyroNewPSs with P/O ratio from 3:20 to 5:20, supported by minor fluctuations of their hydrodynamic diameter and PDI within two months' storage.
Figure 8:
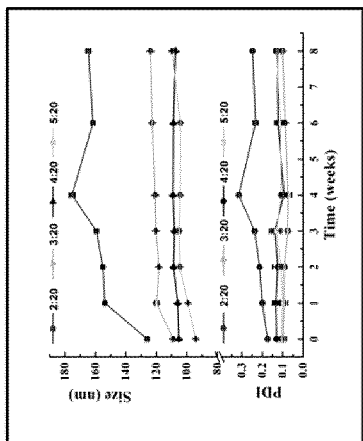
Figure 8:
Figure 9:
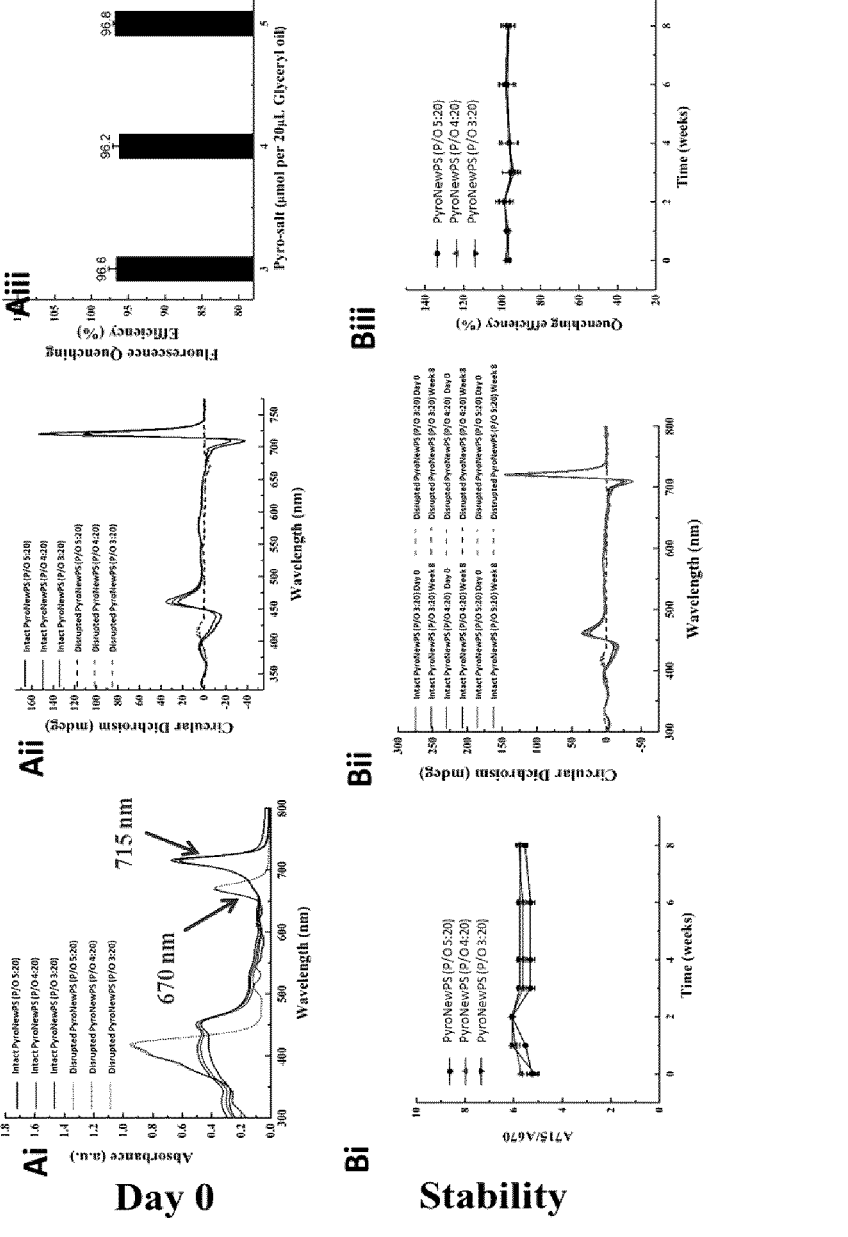
FIG. 9. The Optical properties of various fresh prepared PyroNewPSs (the P/O ratio from 3:20 to 5:20) (A) and their optical stability in 8 weeks storage at 4° C. (B) were further examined by UV-vis spectra (Ai), ratio of absorption of J-aggregate (715 nm) band/monomer band (670 nm) (Bi), CD spectra (Aii and Bii), and fluorescence quenching efficiency (Aiii and Biii). The optical properties of PyroNewPSs in 1% (v %) of Triton X-100, as NewPS-disrupted sample, were also measured as control and for determining the fluorescence quenching efficiency (%): the integrity of fluorescence signal of intact NewPS from 600 nm to 800 nm divided by that of the disrupted NewPS. The results demonstrated that the order aggregation (J-aggregation) of pyro-salt was formed in the NewPS and those PyroNewPSs with the P/O ratio of 3:20 to 5:20 was very stable during storage.
Figure 10:
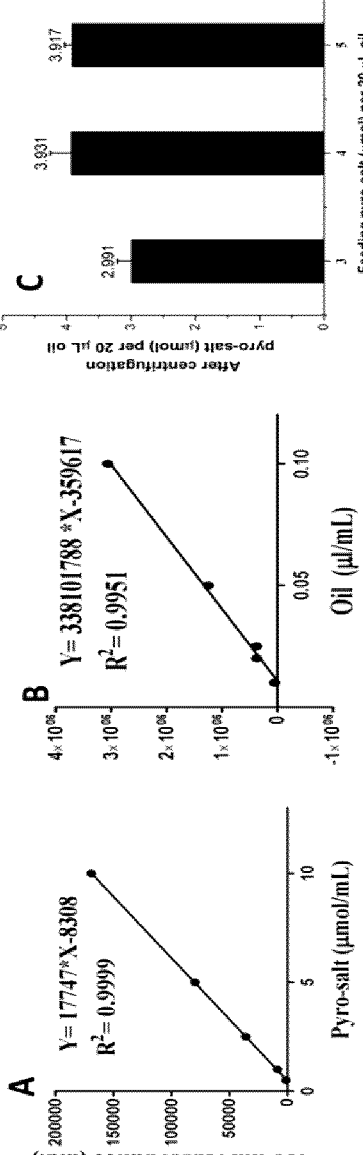
FIG. 10. Quantification of pyro salt/glyceryl oil in final PyroNewPS formulation after gravitational separation (30,000 RPM, for 3 hr) using uPLC method. The standard curve of pyro-salt (A) and oil (B) by uPLC method; The detected P/O ratio (C) compared with initial feeding P/O ratio, indicating the optimized PyroNewPS with P/O of 4:20.
Figure 11:
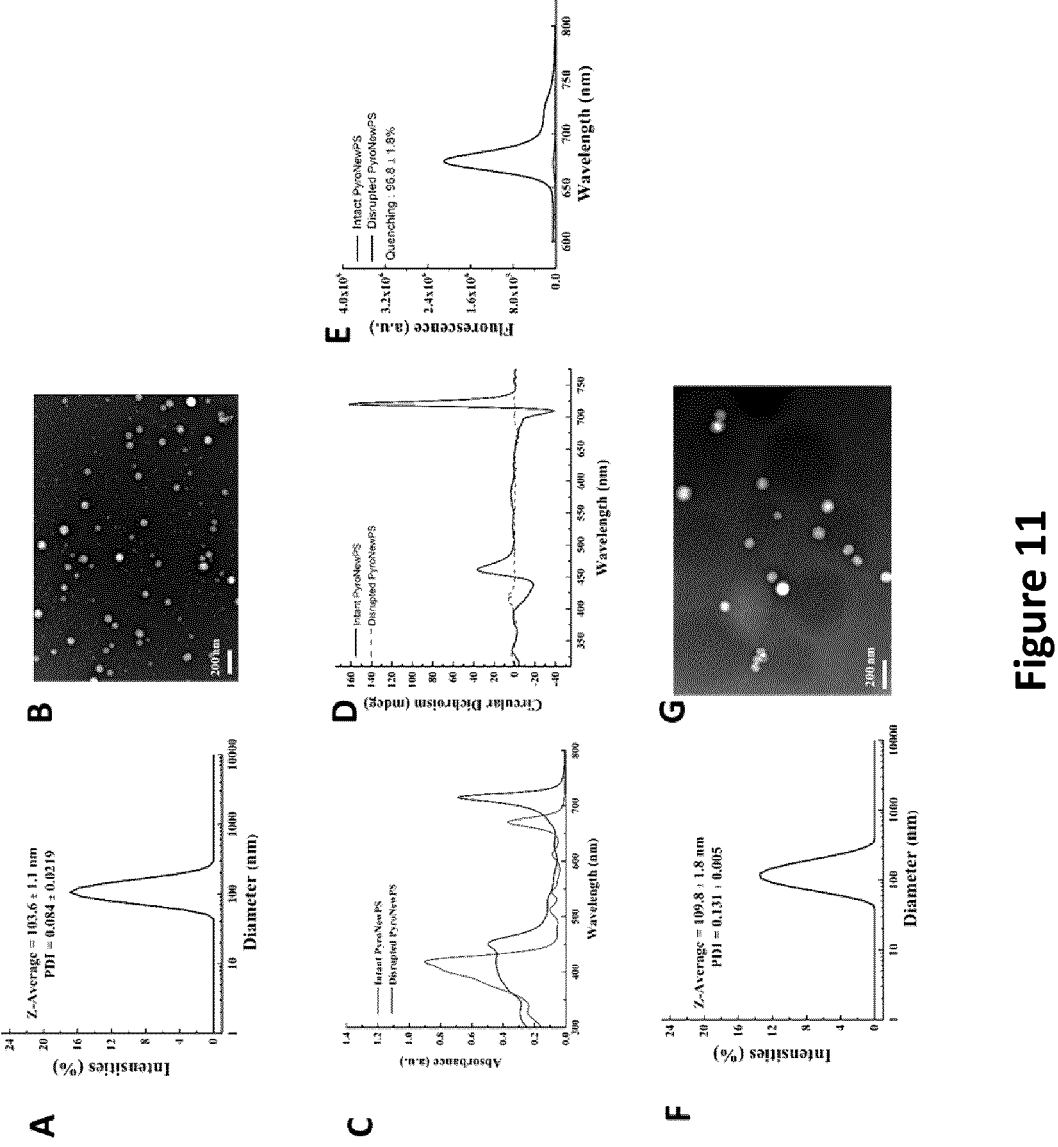
FIG. 11. The characterization of the PyroNewPS after gravitational purification (30,000 RPM, for 3 hr): The DLS profile (A), TEM image (B), and its absorption spectrum (C), CD spectrum (D), and fluorescence spectrum (E) compared with its nanostructure-disrupted sample; The purified PyroNewPS showed high storage stability, evidence by its DLS profile (F) and TEM image(G) after 8-weeks storage at 4° C.

The first prototype of NewPS was formulated by using pyropheophorbide a (Pyro) mono-sodium salt (Pyro-salt) to stabilize the glyceryl trioctanoate oil core. Pyro-salt was selected because of its amphiphilicity with a hydrophobic porphyrin ring and a hydrophilic head of carboxylic acid salt (FIG. 1Ai), as well as its affinity to water-oil interface of lipid nanoparticles.[9] Glyceryl trioctanoate with molecular structure like the food fat used in food grade emulsion,[10] was chosen as a model oil phase. The NewPS was produced by simply hydrating a film of porphyrin salt & oil mixture under sonication to create oil-in-water microemulsion, followed by reducing size to nanoscale by microfluidizer (FIG. 5). The transmission electronic microscopy (TEM) imaging (FIG. 1Ai) and dynamic light scattering (DLS) measurement (FIG. 6A) revealed that the PyroNewPS has monodispersed spherical shell-core structure with main size ~100 nm in diameter. Interestingly, the color of intact PyroNewPS in PBS was visually distinct from its nanostructure-disrupted sample in detergent (FIG. 6B). Further absorption spectra measurement revealed that the PyroNewPS generated a narrow, red-shifted (from 671 nm to 715 nm) and increased Q-band absorbance when compared with the PyroNewPS-disrupted sample (FIG. 1Aii), indicating that Pyro-salt formed order J-aggregation in the PyroNewPS. This significant red-shift (44 nm) absorption might be attributed to the extended π-interactive system.[9] In consistency, a distinct cotton split was detected in the circular dichroism (CD) spectra at the corresponding red-shift absorbance, confirming the order aggregation of Pyro-salt in intact NewPS (FIG. 1Aiii).[11] In addition, the fluorescence of Pyro-salt was highly quenched in the intact PyroNewPS (above 96% quenching efficiency (FIG. 1Aiv), and could be effectively restored when the nanostructure was forced to be disruption, which potentiates low background fluorescence imaging in biomedical application. The PyroNewPS formulation was optimized by adjusting a various ratio of porphyrin content (P) to oil volume (O) (mol/L), in a range of 1:20 to 5:20. The formed PyroNewPSs were subjected to morphology, size distribution and optical properties measurement (FIG. 7) and the results suggested that sufficient amount of Pyro-salt (P/O>2:20) was required for forming a stable PyroNewPS. In addition, PyroNewPSs with P/O ratio from 3:20 to 5:20 showed high storage stability within 2 months at 4° C., supported by minor changes on their morphology, size, and size distribution (FIG. 8) as well as optical properties (FIG. 9). As the PyroNewPS has a low-density oil core of glyceryl trioctanonate (d=0.956 g/mL), a mechanical centrifugation method (30,000 RPM, 3 hr) was applied to condense nanoparticles from PBS continuous phase for PyroNewPS purification. After centrifugation, excess pyro-salt was separated from the PyroNewPS when the initial P/O ratio is over 4:20 (FIG. 10), thus PyroNewPS with P/O ratio of 4:20 was chosen as the optimal formulation for the following study. Importantly, high speed centrifugation did not cause obvious change on size, PDI, morphology (FIG. 11A-B), and optical property (FIG. 11C-E) of the optimized PyroNewPSs, indicating their good stability under gravitational purification. As expected, the purified PyroNewPSs possess storage stability at 4° C. for at least 2 months (FIG. 11F-G).

Figure 12:
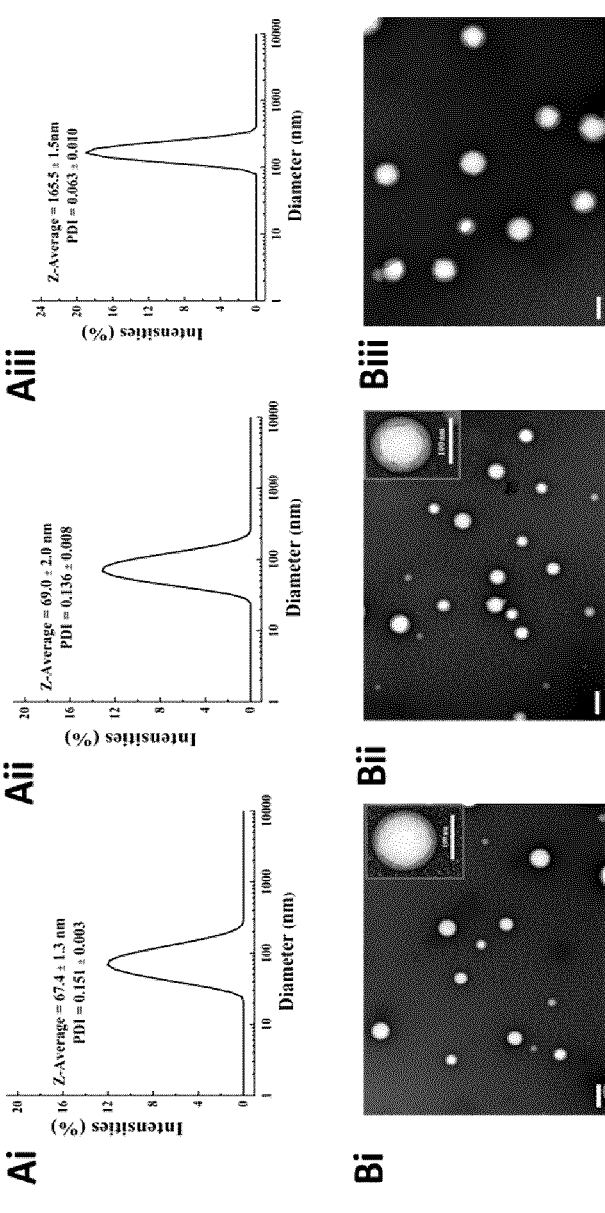
FIG. 12. The DLS profile (A) and TEM images (B) of Ce6NewPS with P/O ratio of 4:20: the fresh-made Ce6NewPS (Ai, Bi); the Ce6NewPS after gravitational purification (30,000 RPM, for 3 hr) (Aii, Bii); the purified Ce6NewPS after storage at 4° C. for 8 weeks (Aiii, Biii). Scale bar: 100 nm.

To investigate if NewPS platform can be generalized to other porphyrin salts, chlorin e6 (Ce6) tris-sodium salt with three hydrophilic heads was used to stabilize glyceryl trioctanoate for NewPS formation (FIG. 1B). As expected, a stable Ce6NewPS was formed at the same P/O ratio of 4:20 (FIG. 1Bi, FIG. 12Ai). Interesting, Ce6-salt did not form a J-aggregation assembly that appeared in PyroNewPS, evidenced by the lack of red-shifted absorbance and distinct cotton split in its CD spectrum (FIG. 1Bii,iii). The fluorescence quenching efficiency was also reduced (FIG. 1Biv). The Ce6NewPS remained morphological stable through gravitation separation and during storage (FIG. 12Aii, Bii, Aiii, Biii), supporting it as a stable nanoemulsion. Its size slightly increased during storage (150-160 nm at age of 8 weeks, FIG. 12Aiii, Biii), which was probably due to multiple hydrophilic heads of Ce6 involved in NewPS stabilization. This resulted in the formation of non-J-aggregate associated assembly that underwent a conformational change on the shell of NewPS. Strikingly, replacing Pyro-salt with Ce6-salt maintained NewPS nanostructure stability while eliminating the J-aggregate formation, suggesting a porphyrin-dependent optical tunability.

Figure 2:
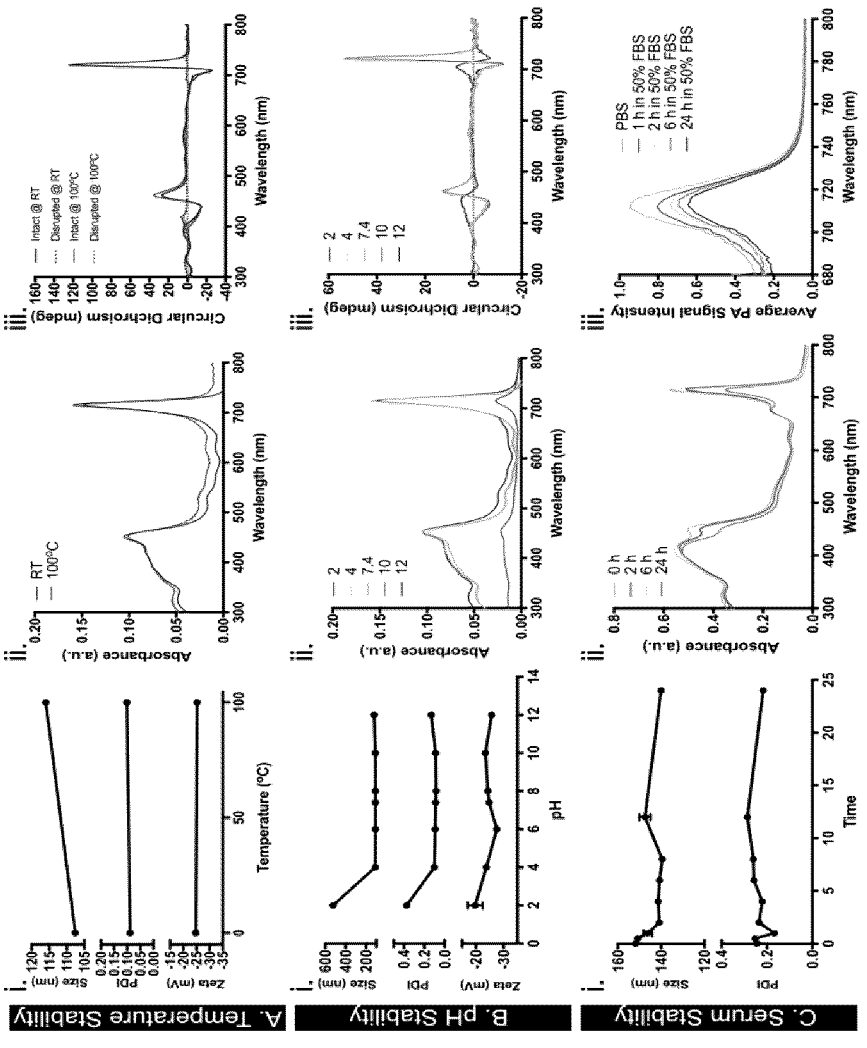
FIG. 2. The colloidal stability of PyroNewPS against (A) temperature change, (B) pH change, and (C) in serum condition were monitered by the physical and optical properties, including the changes in size, zeta potential and PDI (Ai, Bi,Ci); absoption spectra (Aii, Bii,Cii), CD spectra (Aiii, Biii), PA signal (Ciii), and fluorescence quenching efficiency (Aiv, Biv,Civ).
Figure 13:
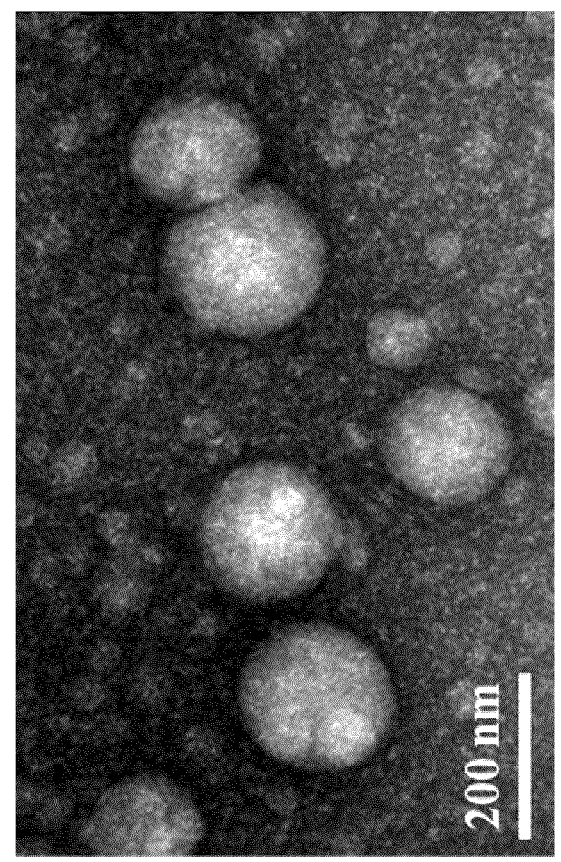
FIG. 13. TEM image of PyroNewPS at pyro concentration of 200 μM after 24 hr incubation with 50% FBS in PBS.

Next, the colloidal stability of PyroNewPS against temperature and pH changes was evaluated.[12] As shown in FIG. 2A-2B, heating to 100° C. and changing pH from 4 to 12 resulted in minimal changes on the physical and optical properties of PyroNewPS. These data together with their high stability under gravitational purification suggest PyroNewPS has high colloidal stability. The serum stability was further evaluated in PBS containing 50% FBS. As shown in FIG. 2Ci, no significant changes on size and fluorescence quenching efficiency were observed during 24 hr incubation and their spherical structure were maintained (FIG. 13), suggesting that PyroNewPS kept its colloidal stability in serum within 24 hr. However, the J-aggregation band's intensity decreased gradually with time to 82% and 59% respectively, at 6 hr and 24 hr post-incubation (FIG. 2Cii). Nevertheless, such optical stability is sufficient to enable J band-specific photoacoustic signal (remaining over 60%) (FIG. 2Ciii) at 24 hr post-incubation for in vivo imaging application.

Figure 3:
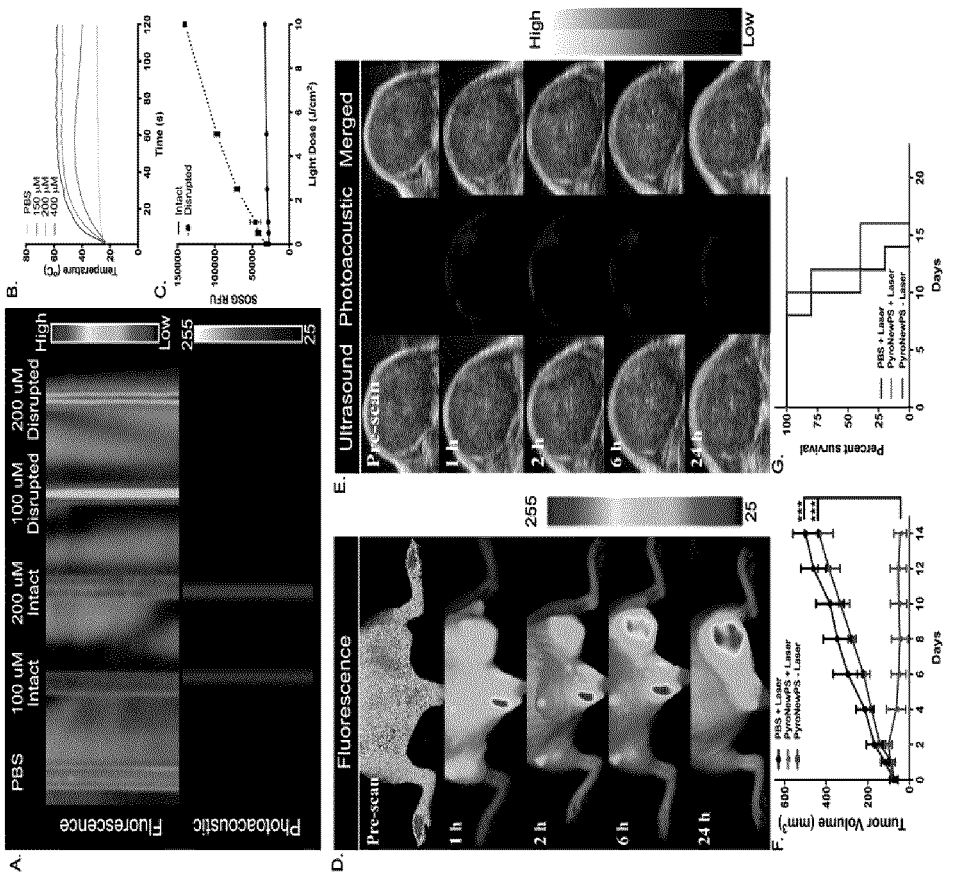
FIG. 3. Multimodality of PyroNewPS on (A) photoacoustic imaging and fluorescence imaging, (B) phototermal ability; and (C) singlet oxygen generation. In vivo photoacoustic imaging (PAI) (D) and fluorescence imaging (E) of KB tumor on mouse model post intravanous injection of PyroNewPS. In vivo PDT efficacy on KB tumor-bearing mice post treatment: Tumor growth curve (G) and Survival curve (F) (***represents $p<0.001$ by one-way ANOVA test).
Figure 14:
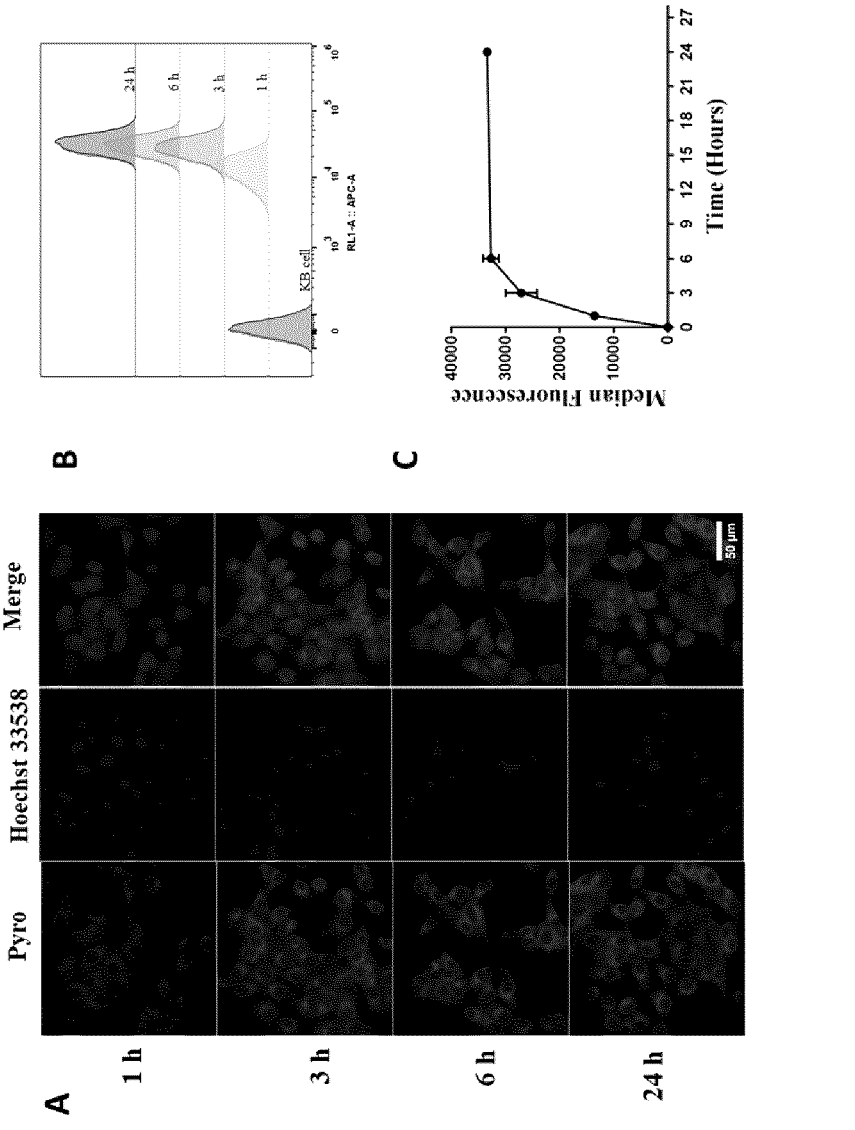
FIG. 14. The intracellular uptake of PyroNewPS: the fluorescence microscope imaging of KB cells after incubation with PyroNewPS for 1 hr, 3 hr, 6 hr and 24 hr, respectively (A). The intracellular uptake of PyroNewPS in KB cells at different time points was measured by Flow cytometry analysis (B) and quantified by the median fluorescence signal of Pyro (C).
Figure 15:
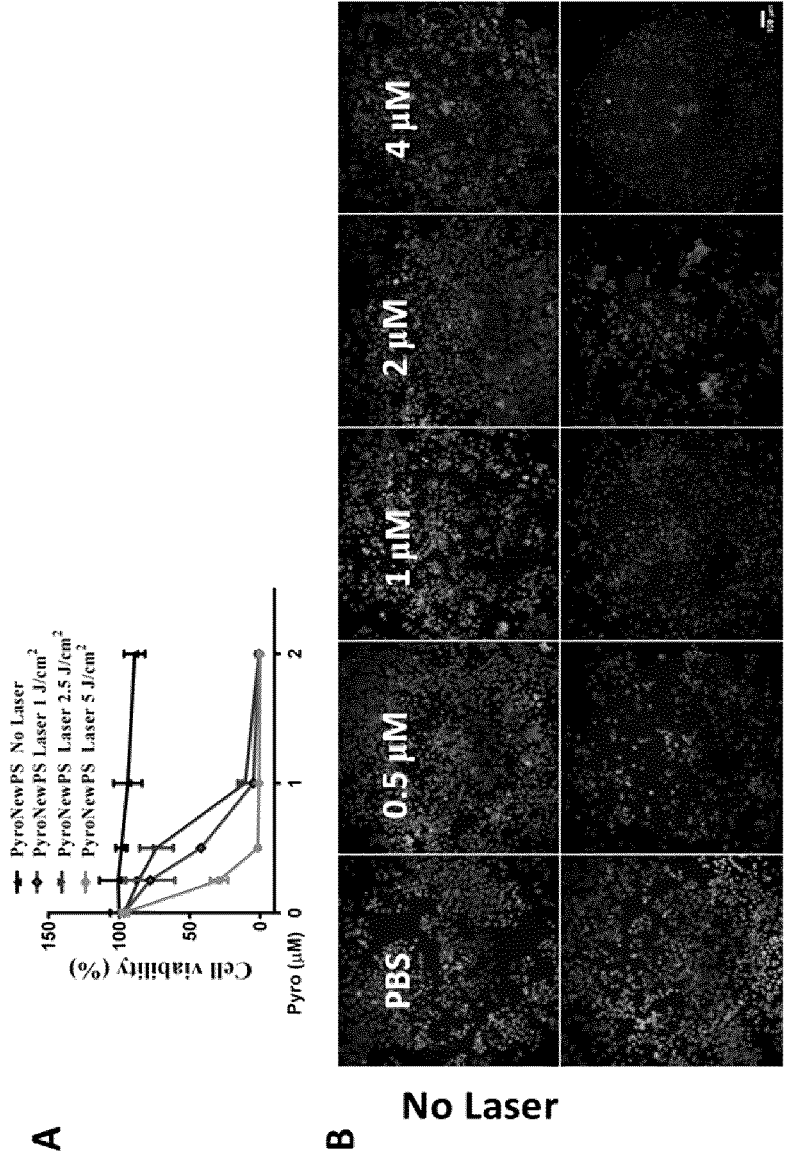
FIG. 15. The photodynamic ability of PyroNewPS was evaluated on KB cells after incubation with PyroNewPS at different concentration and subjected to a 671 nm laser treatment. The MTT assay was used to quantify the cell viability and normalized to the cell control without treatment. Mean±S.D. (n=4) (A). Live/dead cell images of KB cells after incubation with PyroNewPS at different concentration and exposed to the 671 nm laser at the power density of 2.5 J/cm$^2$. Viable cells were stained green with calcein-AM, and dead cells were stained red with Ethd-1 (B). scale bar=100 μm.
Figure 16:
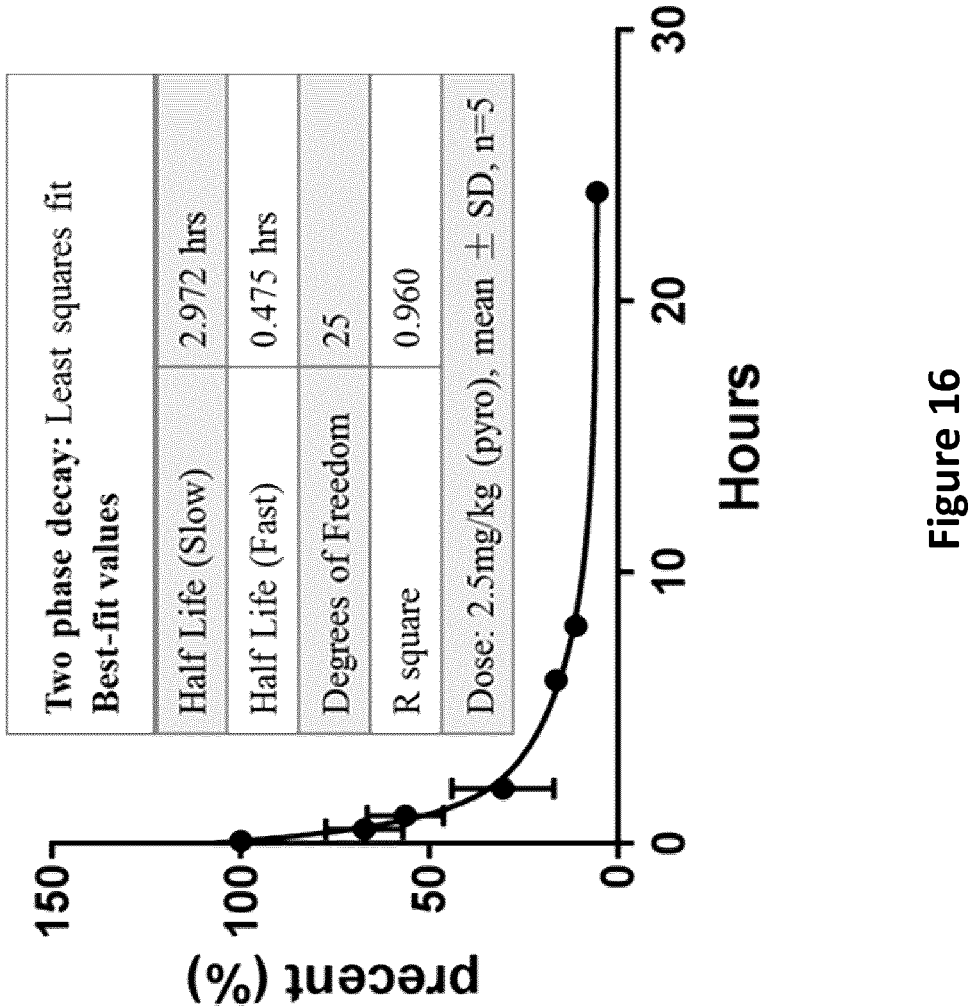
FIG. 16. The blood clearance curve of PyroNewPS.
Figure 17:
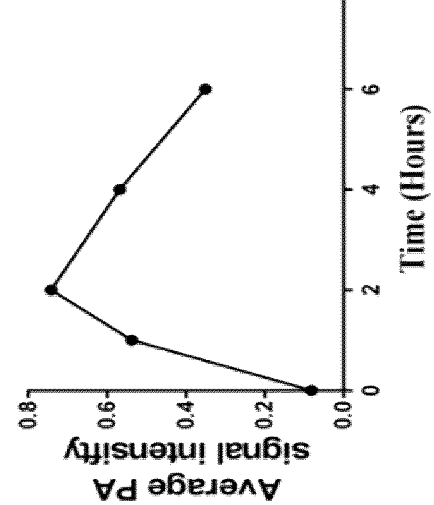
FIG. 17. PA value of tumor before and at different time points post intravenous administration of PyroNewPS FIG. 18. The characterization of PyroNewPS(Lipiodol) with P/O ratio of 4/20. Its size and morphology were measured by DLS (A) and TEM image (B). The optical characters of intact (in PBS) and disrupted (in 1 v/v % triton X-100) PyroNewPS(Lipiodol) by UV-vis spectra (C), CD spectroscopy (D), and spectrofluorometry (E).
Figure 17:
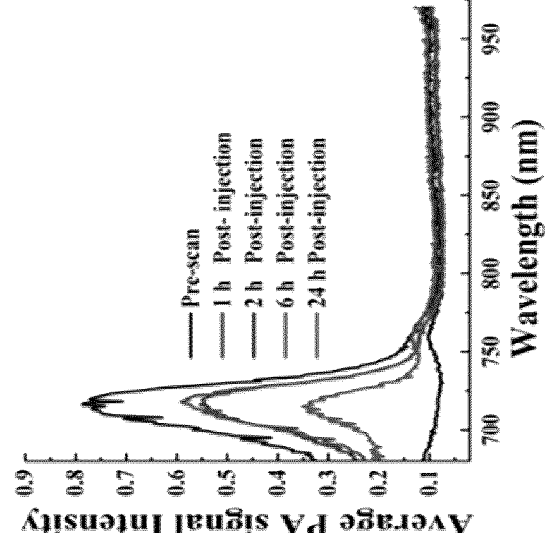

We next investigated PyroNewPS for multimodality optical imaging. As expected, intact PyroNewPS displayed negligible fluorescence (FIG. 3A, top), while exhibited strong photoacoustic signal at 715 nm with a strong concentration-dependent positive correlation (FIG. 3A, bottom). Moreover, significant temperature increase was detected upon laser irradiation at 690 nm (FIG. 3B). These data suggested that PyroNewPS absorbed laser energy and efficiently converted to heat, resulting in photoacoustic (PA) imaging and photothermal efficacy at red-shifted wavelength.[13] When the NewPS was disrupted, the 715 nm photoacoustic signal was diminished while significant monomeric porphyrin's fluorescence (675 nm) was restored (FIG. 3A) and effective singlet oxygen generation (FIG. 3C) were detected under 671 nm laser irradiation, thus potentiating low-background fluorescence imaging and activatable PDT. The intracellular uptake of PyroNewPS was monitored by Pyro fluorescence under microscopy and quantified by flow cytometry and its PDT efficacy was further examined upon 671 nm laser irradiation. The results (FIG. 14) demonstrated that Pyro-NewPS was efficiently taken up by cancer cells and eventually disrupted to restore Pyro fluorescence and photoreactivity to cause potent PDT response (FIG. 15). Attribute to their effective cell uptake, acceptable serum stability (FIG. 2C) and practical circulation half-life time (FIG. 16), the in vivo fluorescence imaging and PA imaging of PyroNewPS was further investigated on mice bearing KB cell xenografts. As shown in FIG. 3D, a low fluorescence signal was detected in tumor at 2 hr post intravenously administration, when a maximum PA signal at 715 nm was reached (FIG. 3E, FIG. 17), indicating that the PyroNewPS rapidly accumulated in the tumor and kept mainly in intact form within 2 hr post injection for significant PA signaling. After 24 hr injection, high tumor fluorescence signal and low tumor PA signal were observed due to the dissociation of PyroNewPS that leaded to the restoration of monomeric Pyro's photoactivities. Therefore, the fluorescent tumors subsequently received localized PDT laser treatment (671 nm, 100 mW/cm², 135 J/cm², n=5). Two control groups: PyroNewPS/no-laser and PBS/laser were also included in the study. The tumor growth curves generated by longitudinally monitoring the tumor growth post treatment (FIG. 3G) revealed that PyroNewPS-PDT significantly suppressed tumor growth. (***represents $p<0.001$ by one-way ANOVA test) and resulted in even complete inhibition with 100% survival rate at day 20 post treatment (FIG. 3F). In contrast, the control groups that received either the PBS/laser or PyroNewPS/no laser (n=5) showed exponential tumor growth (FIG. 3G) indicating that neither of them induced significant therapeutic effects and all animals reached the end point (tumor volume>400 mm³) before or at day 16 (FIG. 3F). Therefore, PyroNewPS exhibited unique structure-dependent biophotonic functions' switch of the PyroNewPS-intact (photoacoustic and PTT at 715 nm) and PyroNewPS-disrupted (activatable fluorescence and PDT at 671 nm) for real-time multi-modality imaging it's in vivo behavior and guiding effective PDT.

Figure 18:
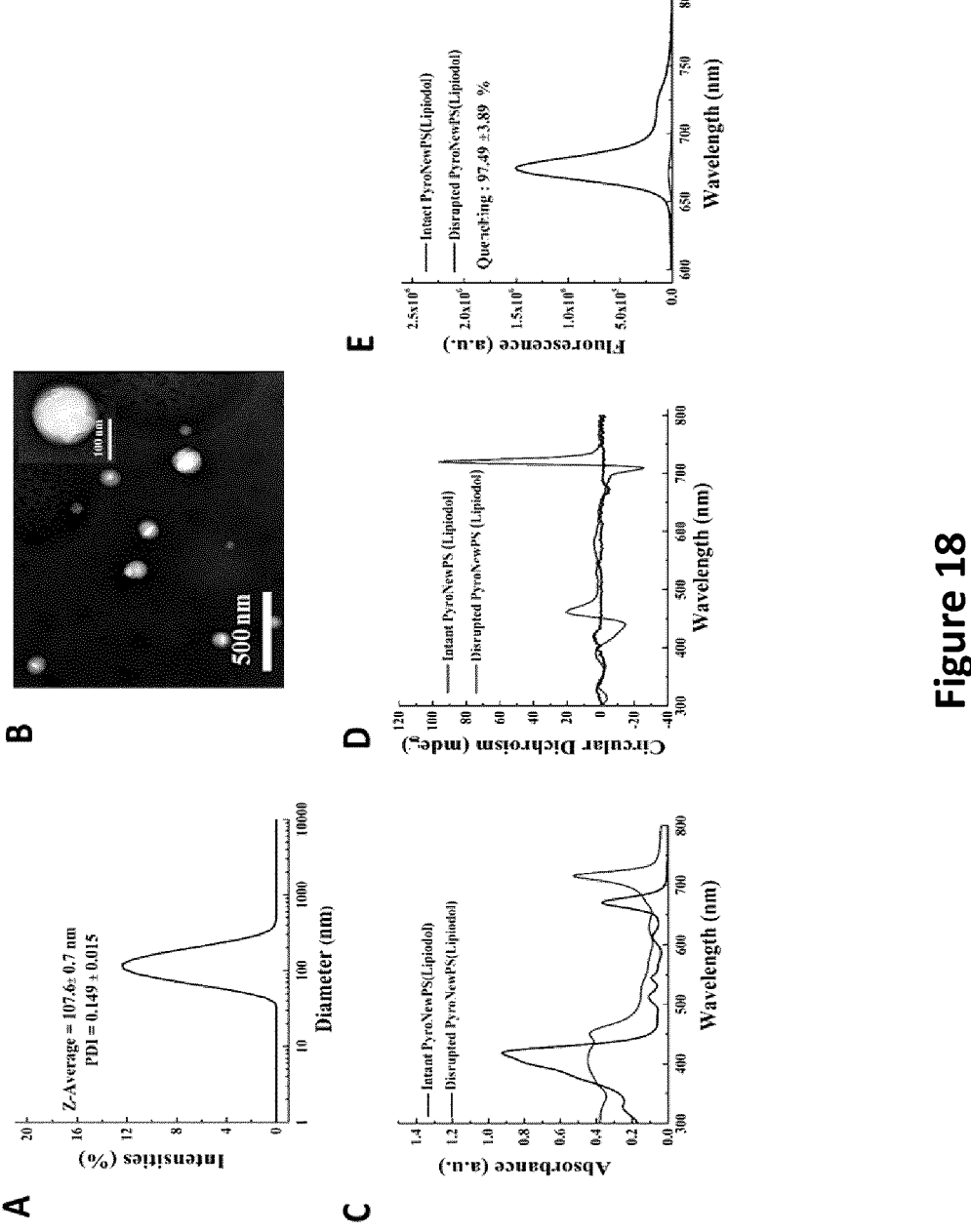
Figure 19:
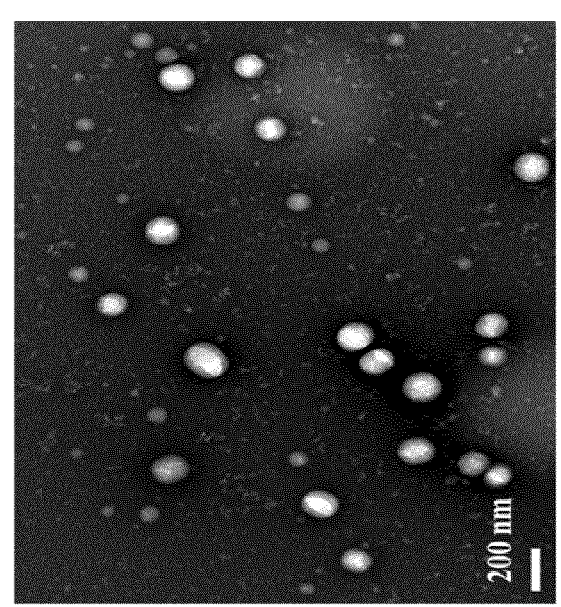
FIG. 19. The size storage stability of PyroNewPS(Lipidol) in 8 weeks at 4° C. (A). TEM image of PyroNewPS (Lipidol) after 8-weeks storage (B).
Figure 19:
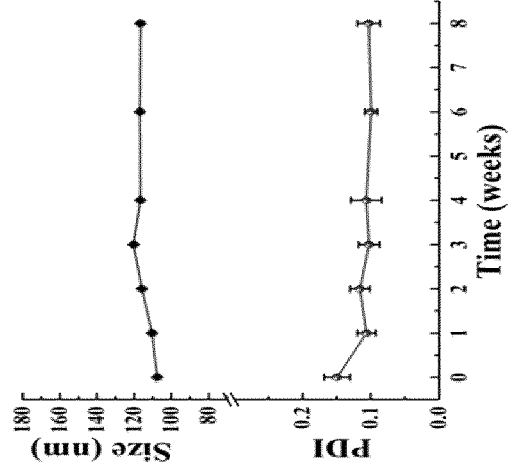
Figure 19:
Figure 20:
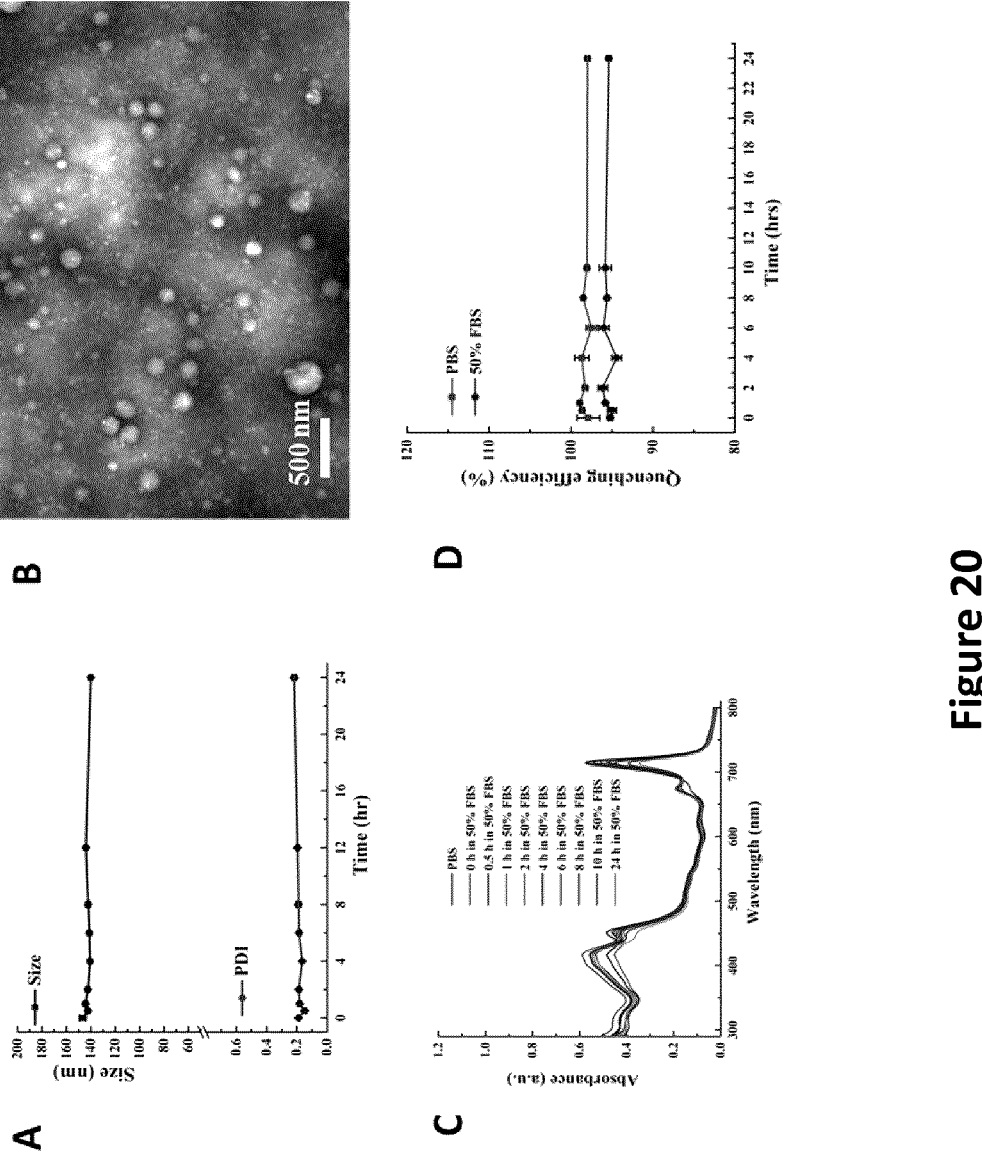
FIG. 20. Serum stability of PyroNewPS(Lipiodol) at pyro concentration of 200 μM incubated with 50% FBS in PBS. Size and PDI changes with time were monitored by DLS (A); TEM image at 24 hr post serum incubation (B); the optical properties change with time were determined by UV absorbance spectrum (C) and fluorescence quenching efficiency (D).

We also demonstrated that the oil core is tunable in NewPS platform. When replacing glyceryl trioctanonate (d=0.956 g/mL), with a high density Lipiodol (d>1.2 g/mL) as oil core matrix in PyroNewPS construction, a stable PyroNewPS(Lipiodol) was formed. As expected, the formulation showed similar properties as the standard PyroNewPS in morphology (e.g. narrow size distribution, spherical structure, FIG. 18A-B), Pyro J-aggregate optical property (FIG. 18C-E), stability (FIG. 19A-B) and serum stability (FIG. 20A-D). In addition, PyroNewPS(lipiodol) afforded additional CT contrast. A phantom imaging study showed a positive linear correlation between CT signal value (HU) and the NewPS's concentration (FIG. 4A top, FIG. 4B), corresponding with a linear correlation of PA value versus NewPS's concentration (FIG. 4A bottom, FIG. 4C), leading to the potential of PyroNewPS(Lipiodol) for dual modality CT/PA imaging.

Figure 4:
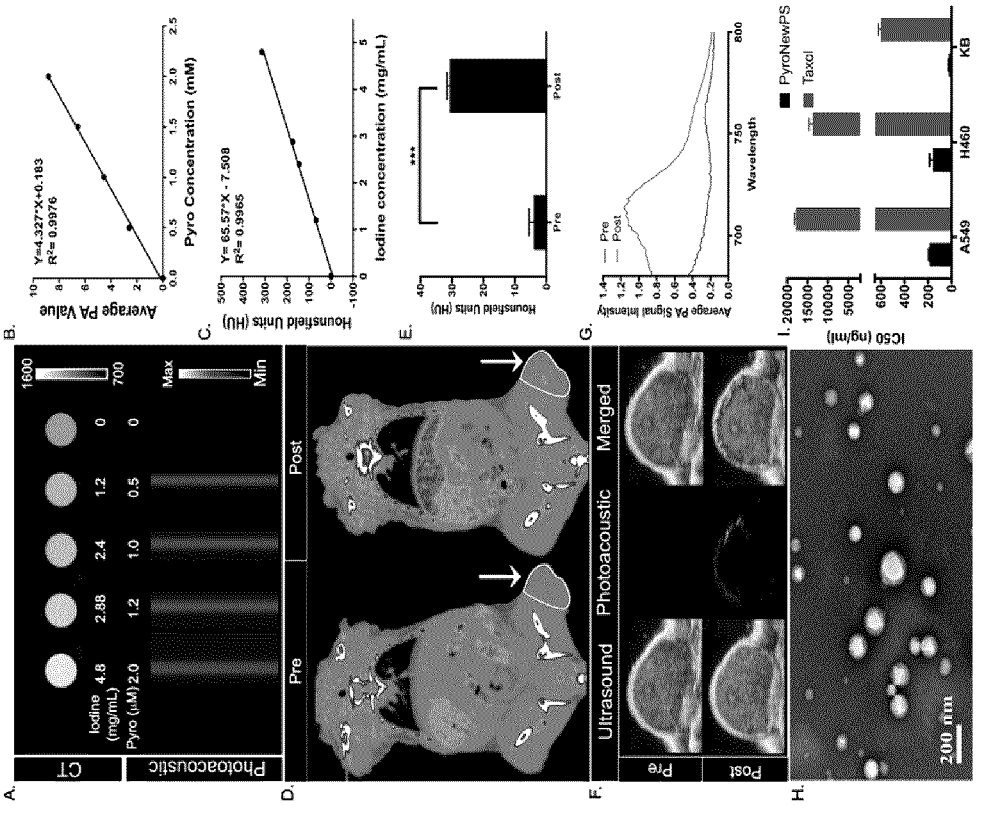
FIG. 4. A phantom CT/PA imaging (A) showed positive linear concentration-depedent (B) CT signal correlation and (C) PA signal correlation. In vivo whole body CT imaging (D) and tumor PA imaging (F) of mouse at 2 hr post injection of PyroNewPS(Lipidol). (E-G) the signal value quantification of CT and PA imaging around tumor region prior and post injection were compared (***represents $p<0.001$ by two-tailed t-test). (H) the TEM image of PyroNewPS&PTX and (I) the IC50 of PyroNewPS@PTX vs.Taxol to various cancer cells including A549, H460 and KB cells.

The in vivo CT/PA imaging ability of Pyro-NewPS(Lipiodol) was next investigated on the nude mice bearing xenografted KB tumor. Time-depended tumor CT and PA imaging were carried out after injection of PyroNewPS (Lipidol) with Pyro dose of 57.9 mg/kg and Iodine dose of 250 mg/kg. Significant CT and PA signal enhancement was both detected at 2 hr post injection (FIGS. 4D &F). The CT and PA value quantification in tumor region further validated the dual modality function of PyroNewPS(Lipidol) (FIGS. 4E&4G).

Figure 21:
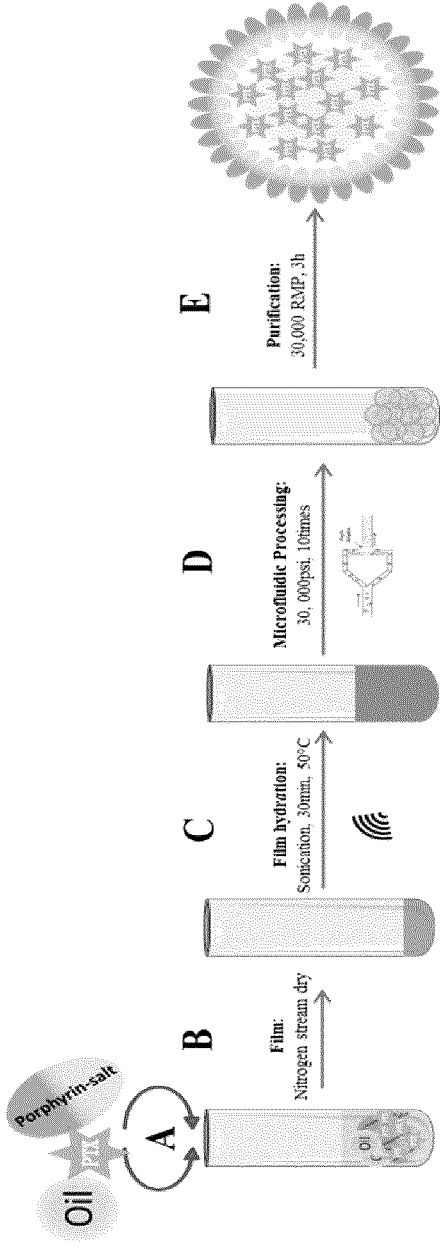
FIG. 21. The schematic outline of the preparation of PTX loaded PyroNewPS. Porphyrin-salt, oil and PTX were dissolved in CHCl$_3$ and MeOH (9:1=CHCl$_3$:MeOH) (A), dried under N$_2$ stream>3 hr (B). PBS (3 mL) was added and the film was bath sonicated at 50° C. for 30 min until the solution was clear (C). The solution passed through a microfluidiser at 30,000 psi for 10 times (D). The PyroNewPS@PTX was purified by centrifugation method (30,000 RPM, 3 hr) (E).

As NewPS has a high weight fraction of oil matrix (>80 w %), we investigated its capability for delivery drugs. The standard PyroNewPS was investigated for delivery a proxy drug, paclitaxel (PTX). The synthesis of PTX loaded PyroNewPS (PyroNewPS@PTX) was illustrated in FIG. 21. With the increase of loading amount of PTX, the hydrodynamic diameter of the NewPS were gradually increasing, while PTX entrapment efficiency were non-linearly decreasing (FIG. 22). The drug-loading capacity and entrapment efficiency was analyzed by uPLC assay. The drug-loading capacity could reach 85% when initially adding PTX≤0.8 mg in total 22 mg formulation, resulting in 130 nm size with spherical and uniform shell-core structure (FIG. 4H) and similar optical properties as the standard PyroNewPS (FIG. 23Ai-Aiii). The formed PyroNewPS@PTX were stable during 8 weeks' storage with minor changes in size, size distribution and morphology. As shown in FIG. 23Bi-Biii, the incorporation of PTX in PyroNewPS had no effect on the optical property. The chemotherapeutic efficacy was evaluated by measuring its IC50 against different cancer cells. When compared with a clinical PTX formulation, Toxal, the IC50 of PyroNewPS@PTX to KB, A549 and H460 cells was decreased about 94-fold, 85-fold and 24-fold respectively (FIG. 4I, FIG. 24). Therefore, NewPS can service as an efficiency drug delivery vehicle for cancer treatment.

In summary, a novel nanoemulsion with porphyrin shell (NewPS) was created as a simplest multifunctional nanoemulsion system known to date. The porphyrin salt shell allowed the encapsulation and stabilization of the oil core to offer monodispersed spherical nanostructure with excellent colloidal stability. The intrinsic multimodality of porphyrins and the nanostructure drove the NewPS multifunctionality for imaging and phototherapy. Moreover, the oil core enabled a matrix for efficient hydrophobic molecules encapsulation, paving a way for many hydrophobic chemotherapeutic drugs' delivery. The multimodality of NewPSs could be engineered by simple switching either porphyrin salt shell or oil matrix, as well as various drug loading.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST

[1] a) H. Bu, X. He, Z. Zhang, Q. Yin, H. Yu, Y. Li, International journal of pharmaceutics 2014, 471, 206-213; b)M. Jaiswal, R. Dudhe, P. Sharma, 3 Biotech 2015, 5, 123-127.
[2] a) C. A. Dehelean, S. Feflea, S. Ganta, M. Amiji, Journal of biomedical nanotechnology 2011, 7, 317-324; b) S. Ganta, M. Talekar, A. Singh, T. P. Coleman, M. M. Amiji, Aaps Pharmscitech 2014, 15, 694-708; c) V. K. Rai, N. Mishra, K. S. Yadav, N. P. Yadav, Journal of controlled release: official journal of the Controlled Release Society 2018, 270, 203-225; d) Y. Singh, J. G. Meher, K. Raval, F. A. Khan, M. Chaurasia, N. K. Jain, M. K. Chourasia, Journal of controlled release, 2017, 252, 28-49.
[3] C. O. Silva, J. O. Pinho, J. M. Lopes, A. J. Almeida, M. M. Gaspar, C. Reis, Pharmaceutics 2019, 11. doi: 10.3390/pharmaceutics11010022.
[4] a) D. A. Fernandes, D. D. Fernandes, Y. Li, Y. Wang, Z. Zhang, D. r. Rousseau, C. C. Gradinaru, M. C. Kolios, Langmuir 2016, 32, 10870-10880; b) A. Gianella, P. A. Jarzyna, V. Mani, S. Ramachandran, C. Calcagno, J. Tang, B. Kann, W. J. Dijk, V. L. Thijssen, A. W. Griffioen, ACS nano 2011, 5, 4422-4433; c) S. Ganta, A. Singh, N. R. Patel, J. Cacaccio, Y. H. Rawal, B. J. Davis, M. M. Amiji, T. P. Coleman, Pharmaceutical research 2014, 31, 2490-2502; d) N. R. Patel, A. Piroyan, A. H. Nack, C. A. Galati, M. McHugh, S. Orosz, A. W. Keeler, S. O'Neal, W. C. Zamboni, B. Davis, Molecular pharmaceutics 2016, 13, 1996-2009; e) S. J. Lee, P. H. Schlesinger, S. A. Wickline, G. M. Lanza, N. A. Baker, The journal of physical chemistry. B 2011, 115, 15271-15279; f) N. R. Patel, A. Piroyan, S. Ganta, A. B. Morse, K. M. Candiloro, A. L. Solon, A. H. Nack, C. A. Galati, C. Bora, M. A. Maglaty, S. W. O'Brien, S. Litwin, B. Davis, D. C. Connolly, T. P.

Coleman, Cancer biology & therapy 2018, 19, 554-564; g) S. K. Patel, W. Beaino, C. J. Anderson, J. M. Janjic, Clinical immunology 2015, 160, 59-70.
[5] P. A. Jarzyna, T. Skajaa, A. Gianella, D. P. Cormode, D. D. Samber, S. D. Dickson, W. Chen, A. W. Griffioen, Z. A. Fayad, W. J. Mulder, Biomaterials 2009, 30, 6947-6954.
[6] L. Yan, A. Amirshaghaghi, D. Huang, J. Miller, J. M. Stein, T. M. Busch, Z. Cheng, A. Tsourkas, Advanced functional materials 2018, 28, 1707030.
[7] a) A. Nel, T. Xia, L. Madler, N. Li, science 2006, 311, 622-627; b) M. A. Dobrovolskaia, S. E. McNeil, Nature nanotechnology 2007, 2, 469.
[8] a) M. Rajora, J. Lou, G. Zheng, Chemical Society Reviews 2017, 46, 6433-6469; b) Y. Li, T. Y. Lin, Y. Luo, Q. Liu, W. Xiao, W. Guo, D. Lac, H. Zhang, C. Feng, S. Wachsmann-Hogiu, J. H. Walton, S. R. Cherry, D. J. Rowland, D. Kukis, C. Pan, K. S. Lam, Nature communications 2014, 5, 4712; c) Y. Zhou, X. Liang, Z. Dai, Nanoscale 2016, 8, 12394-12405.
[9] L. Cui, D. Tokarz, R. Cisek, K. K. Ng, F. Wang, J. Chen, V. Barzda, G. Zheng, Angewandte Chemie International Edition 2015, 54, 13928-13932.
[10] Y. Tan, K. Xu, C. Niu, C. Liu, Y. Li, P. Wang, B. P. Binks, Food Hydrocolloids 2014, 36, 70-75.
[11] E. Huynh, B. Y. Leung, B. L. Helfield, M. Shakiba, J.-A. Gandier, C. S. Jin, E. R. Master, B. C. Wilson, D. E. Goertz, G. Zheng, Nature nanotechnology 2015, 10, 325.
[12] S. Khurana, N. Jain, P. Bedi, Life sciences 2013, 92, 383-392.
[13] J. F. Lovell, C. S. Jin, E. Huynh, H. Jin, C. Kim, J. L. Rubinstein, W. C. Chan, W. Cao, L. V. Wang, G. Zheng, Nature materials 2011, 10, 324.

The invention claimed is:

1. A nanoparticle comprising an outer shell comprising a porphyrin salt, an expanded porphyrin salt or an analog of porphyrin salt, around an inner liquid oil phase core, wherein
the ratio of porphyrin (P) to oil (O) volume (mol/L) is equal to or greater than 2:20; and
the porphyrin salt is a salt of a hematoporphyrin, a protoporphyrin, a pyropheophorbide a, a bacteriochlorophyll, a chlorophyll a, a tetraphenylporphyrin, a benzoporphyrin, a verpetorfin, a chlorin, a benzochlorin, a naphthochlorins, a rhodin, a keto chlorin, an azachlorin, a bacteriochlorin, a tolyporphyrin, a benzobacteriochlorin, a deuteroporphyrin, a pemptoporphyrin a phylloerythrin, a porphine, or purpurin 18;
the expanded porphyrin salt is a salt of a texaphyrin, a sapphyrin or a hexaphyrin;
the analog of porphyrin salt is a salt of a porphycene, an inverted porphyrin, a phthalocyanine, a naphthalocyanine, a BODIPY dye, or a cyanine dye; zinc (II) phthalocyanine mono-sodium salt; aza-BODIPY mono-sodium salt; or ICG cyanine salt;
the porphyrin salt is amphiphilic and encapsulates and stabilizes the liquid oil phase core to form a spherical nanoparticle.

2. The nanoparticle of claim 1, wherein the outer shell is a porphyrin salt.

3. The nanoparticle of claim 2 wherein the porphyrin salt, expanded porphyrin salt or analog of porphyrin salt, is the porphyrin salt.

4. The nanoparticle of claim 3, wherein the porphyrin salt is a carboxylate or sulfonate salt.

5. The nanoparticle of claim 1, wherein the outer shell is the expanded porphyrin salt.

6. The nanoparticle of claim 1, wherein the outer shell is the analog of porphyrin salt.

7. The nanoparticle of claim 1, wherein the porphyrin salt is pryopheophorbide a mono-sodium salt.

8. The nanoparticle of claim 1, wherein the porphyrin salt is chlorine6 tris-sodium salt.

9. The nanoparticle of claim 1, wherein the porphyrin salt is bacteriopheophorbide α mono-sodium salt.

10. The nanoparticle of claim 6, wherein the analog of porphyrin salt is zinc(II) phthalocyanine mono-sodium salt.

11. The nanoparticle of claim 6, wherein the analog of porphyrin salt is aza-BODIPY mono-sodium salt.

12. The nanoparticle of claim 6, wherein the analog of porphyrin salt is ICG cyanine salt.

13. The nanoparticle of claim 1, wherein the oil is a modified or hydrolyzed vegetable oil, a natural di- or tri-glyceride; a medium chain triglyceride; a semi synthetic medium chain triglyceride containing compound, a digestible or non-digestible oil or fat.

14. The nanoparticle of claim 13, wherein the oil is olive oil, corn oil, soybean oil, palm oil, animal fat, Lipidol oil, or mineral oil.

15. The nanoparticle of claim 13, wherein the oil is glyceryl trioctanoate oil.

16. The nanoparticle of claim 13, wherein the oil is lipidol.

17. The nanoparticle of claim 1, wherein the nanoparticle is 50 nm-200 nm in diameter.

18. The nanoparticle of claim 17, wherein the nanoparticle is 80 nm-150 nm in diameter.

19. The nanoparticle of claim 18, wherein the nanoparticle is about 100 nm in diameter.

20. The nanoparticle of claim 1, co-loaded with a therapeutic or diagnostic agent.

21. The nanoparticle of claim 20, wherein the therapeutic agent is a chemotherapy agent.

22. The nanoparticle of claim 21, wherein the chemotherapy agent is a taxane.

23. The nanoparticle of claim 20, wherein the loading capacity is about 10%, 20%, 30%, 40%, 50%, 60%, 70%, 80%, or 85%.

24. A composition comprising the nanoparticle of claim 1 and water.

25. The composition of claim 24, being surfactant free.

26. The composition of claim 24, wherein the nanoparticle is in PBS.

27. The composition of claim 24, being a nanoemulsion.

28. The composition of claim 1, wherein the P/O ratio is 2:20 to 5:20.

29. The composition of claim 28, wherein the P/O ratio is about 4:20.

30. A method of performing fluorescence imaging on a target area in a subject comprising:
   a. providing the composition of claim 24;
   b. administering the composition to the subject; and
   c. imaging the target area.

31. A method delivering a diagnostic or therapeutic agent to a subject comprising administering to the subject the composition of claim 24, wherein the nanoparticle has been co-loaded with said diagnostic or therapeutic agent.

* * * * *